US009610209B2

(12) United States Patent
Yasuhara et al.

(10) Patent No.: US 9,610,209 B2
(45) Date of Patent: Apr. 4, 2017

(54) WALKING MOTION ASSIST DEVICE

(71) Applicant: HONDA MOTOR CO., LTD., Tokyo (JP)

(72) Inventors: Ken Yasuhara, Wako (JP); Yosuke Endo, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 641 days.

(21) Appl. No.: 14/068,794

(22) Filed: Oct. 31, 2013

(65) Prior Publication Data

US 2014/0121575 A1 May 1, 2014

(30) Foreign Application Priority Data

Nov. 1, 2012 (JP) ................................ 2012-241939
Nov. 1, 2012 (JP) ................................ 2012-242186

(51) Int. Cl.
*A61F 5/01* (2006.01)
*A61H 3/00* (2006.01)
*A61H 1/02* (2006.01)

(52) U.S. Cl.
CPC ............. *A61H 3/00* (2013.01); *A61H 1/0244* (2013.01); *A61H 2201/164* (2013.01);
(Continued)

(58) Field of Classification Search
CPC .......... A61H 1/00; A61H 1/02; A61H 1/0237; A61H 1/024; A61H 1/0244; A61H 1/0262; A61H 3/00; A61H 2201/16; A61H 2201/1628; A61H 2201/163; A61H 2201/164; A61H 2201/1642; A61H 2201/50; A61H 2201/5005; A61H 2201/5007; A61H 2201/5058; A61H 2201/5061; A61H 2201/5064; A61H 2201/5069; A61H 2201/5071; A61H 2201/5079; A61H 2201/5084; A61H 2203/00; A61H 2203/04; A61H 2203/0406; A61H 2205/00; A61H 2205/10; A61H 2205/102
See application file for complete search history.

(56) References Cited

U.S. PATENT DOCUMENTS

2005/0177080 A1* 8/2005 Yasuhara ............... A61B 5/112 602/16
2009/0062884 A1* 3/2009 Endo .................... A61N 1/0452 607/49
(Continued)

FOREIGN PATENT DOCUMENTS

JP 2004-329520 11/2004
JP 2009-095577 5/2009
(Continued)

OTHER PUBLICATIONS

Japanese Office Action dated Oct. 20, 2015, 5 pages.
Japanese Office Action dated Nov. 10, 2015, 3 pages.

*Primary Examiner* — Steven Douglas
(74) *Attorney, Agent, or Firm* — Rankin, Hill & Clark LLP

(57) ABSTRACT

According to a walking motion assist device 10, an assisting force T of a leg in a standing-leg period is controlled to indicate a greatest value or a maximum value in a first designated period (refer to the one-dot chain line and the two-dot chain line in t=t1 to t2). By doing so, in the first designated period (an initial period or a prior period) of one leg, a translation of a body derived from a floor reaction force acting on the one leg is largely prompted compared to other periods of the standing-leg period. A smooth starting of floor leaving and bending motion of the other leg is prompted so as to follow the translation of the body.

8 Claims, 16 Drawing Sheets

(52) U.S. Cl.
CPC .................. *A61H 2201/165* (2013.01); *A61H 2201/1628* (2013.01); *A61H 2201/1671* (2013.01); *A61H 2201/5007* (2013.01); *A61H 2201/5064* (2013.01); *A61H 2201/5069* (2013.01); *A61H 2201/5084* (2013.01); *A61H 2205/088* (2013.01)

(56) References Cited

U.S. PATENT DOCUMENTS

| | | | | |
|---|---|---|---|---|
| 2009/0227424 A1* | 9/2009 | Hirata | .................. | A61B 5/1038<br>482/7 |
| 2010/0049102 A1* | 2/2010 | Yasuhara | ............. | A61H 1/0244<br>601/5 |
| 2010/0049333 A1* | 2/2010 | Endo | ........................ | A61H 3/00<br>623/27 |
| 2010/0234775 A1* | 9/2010 | Yasuhara | ................. | A61H 3/00<br>601/33 |
| 2011/0264015 A1* | 10/2011 | Endo | .................... | A61H 1/0255<br>601/35 |
| 2012/0215140 A1* | 8/2012 | Hirata | .................. | A61H 1/0244<br>601/35 |
| 2012/0310122 A1* | 12/2012 | Endo | .................... | A61H 1/0244<br>601/35 |

FOREIGN PATENT DOCUMENTS

| | | |
|---|---|---|
| JP | 2010-075658 | 4/2010 |
| WO | 2011/049171 | 4/2011 |

* cited by examiner

WALKING MOTION ASSIST DEVICE

BACKGROUND OF THE INVENTION

Field of the Invention

The present invention relates to a device adapted to assist a walking motion of a creature.

Description of the Related Art

There has been proposed a technical approach for controlling strength of an assisting force in a walking motion cycle in order to prompt smooth walking motion of a creature by the assisting force acted on the creature (refer to Japanese Patent Publication No. 4271713, published on Jun. 3, 2009 (Patent Document 1), hereby incorporated in full by reference).

Specifically, a stretching motion of a leg is assisted by a relatively strong force in a floor-landing state and a stretching motion state of the leg, and as a result, the leg receives relatively strong floor reaction force. This floor reaction force is transferred to the body via the leg in the floor-landing state, thereby prompting translation of the body to the forward. Moreover, by the reflex due to the leg being stretched in the floor-landing state by the assisting force (stretch reflex), a bending motion (a forward motion) of the leg is prompted in the floor-leaving state subsequent to the floor-landing state. Therefore, the periodic walking motion of the creature is assisted so as to prompt not only the stretching motion (a backward motion) of the leg of the creature in the floor-landing state, but also smooth bending motion (the forward motion) of the leg in the floor-leaving state.

However, there still remains a possibility of improvement in the manner of walking motion assisting from the view point of linkage of each motion of a pair of right and left legs of the creature.

SUMMARY OF THE INVENTION

Accordingly, an object of the present invention is to provide a device capable of achieving, in view of a motion state of one leg of a creature, to smoothen a motion of the other leg when assisting a walking motion of the creature. Furthermore, it is an object of the present invention to provide a device capable of assisting the walking motion while attaining stability of a posture of the creature in view of a linkage (correlation) of each motion state of a pair of right and left legs of the creature.

The present invention relates to a device adapted to assist a walking motion of a creature, comprising: an attachment adapted to be attached to a body and each of at least one leg of a creature; at least one actuator configured to transfer motive power to the attachment, and a controller configured to control an operation of the at least one actuator, in which the walking motion of the creature is assisted by acting the motive power of the at least one actuator on the creature via the attachment. The walking motion assist device of the first aspect of the present invention is characterized in that the controller is configured to control a temporal change manner of the motive power of the actuator so that an assisting force or a work in a standing-leg period of the leg indicates a greatest value or a maximum value in a first designated period which is a period from starting of an stretching motion of the leg until a posture thereof coincides with a posture of a basic frontal plane.

According to the walking motion assist device of the first aspect of the present invention, in the first designated period of one leg among the pair of right and left legs of the creature (initial period or prior period of the standing-leg period), the translation of the body derived from the floor reaction force acting on the one leg is largely prompted compared to other period of the standing-leg period. The first designated period of the one leg overlaps at least one of the periods of immediately before or immediately after a time point when the other leg transits from a standing-leg state to a lifted-leg state. Therefore, a smooth start of leaving the floor and the bending motion of the other leg is induced so as to follow the translation of the body. As a result, in view of the motion state of one leg, a smooth motion of the other leg is achieved.

The walking motion assist device of the first aspect of the present invention may be configured to make the assisting force act on both of the pair of right and left legs, or may be configured to make the assisting force act on one leg while not allowing the force derived from the device to act on the other leg. Beside the assisting force, force derived from friction between members of a power transmission mechanism configuring the actuator is also included.

It is preferable that the controller is configured to control the temporal change manner of the motive power of the actuator so that the assisting force or the work in the standing-leg period of the leg is maintained to zero until the standing-leg period terminates, after indicating the greatest value or the maximum value in the first designated period.

According to the walking motion assist device of the above configuration, in the later period of the standing-leg period of one leg, that is, immediately before or after start of the standing-leg period or the first designated period of the other leg, the one leg becomes in a state capable of motion without being restricted by the operation of the actuator. Therefore, in a case the walking motion assist device is configured to act the assisting force on both legs, in the first designated period of the other leg, a smooth start of floor leaving and bending motion of the one leg is prompted following the translation of the body being relatively largely facilitated as described above. As a result, in view of the motion state of one leg, smooth motion of the other leg is attained.

It is preferable that the controller is configured to adjust the greatest value or the maximum value of the assisting force or the work in the first designated period so that an overlapping period of the standing-leg period of each of a pair of right and left legs of the creature approaches zero.

According to the walking motion assist device of the above configuration, it is able to uniformly shorten a both-legs-supported period in which both of the legs are in a standing-leg state, even if the followability of the floor leaving motion of the leg associated with the translation of the body is right-left asymmetry or different due to the individual difference of the creature. Therefore, in the first designated period of one leg, it is able to avoid a situation in which the other leg is dragged due to delay of floor leaving of the other leg. As a result, in view of the motion state of one leg, smooth motion of the other leg is attained.

It is preferable that the controller is configured to control the temporal change manner of the motive power of the actuator so that the assisting force or the work in the lifted-leg period of the leg indicates a greatest value or a maximum value in a second designated period which is a period from a transition of the leg to a stretching motion state from a bending motion state, until it becomes the standing-leg state.

According to the walking motion assist device of the above configuration, in the second designated period of one leg, the translation of the body derived from the floor reaction force acting on the other leg is more prompted compared to other periods of the lifted-leg period. By doing so, immediately after the start of the first designated period continuing from the second designated period of the other leg, the floor reaction force acting on the one leg is increased, thereby the translation of the body similar to the above in the first designated period is further largely facilitated, and a smooth start of floor leaving and bending motion of the other leg is further facilitated. As a result, in view of the motion state of one leg, smooth motion of the other leg is attained.

The walking motion assist device of the second aspect of the present invention is characterized in that the controller is configured to control a temporal change manner of the motive power of the actuator to adjust a length (long/short) of each of a third designated period and a fourth designated period, in a case where an assisting force is acted in a stretching direction of one leg in a standing-leg state among the pair of right and left legs and the assisting force is acted in a bending direction of the other leg in a lifted-leg state, the third designated period being a period in which the assisting force acting on the one leg is stronger than the assisting force acting on the other leg, and the fourth designated period being a period subsequent to the third designated period and in which the assisting force acting on the other leg is stronger than the assisting force acting on the one leg.

According to the walking motion assist device of the second aspect of the present invention, in the third designated period, the center of gravity of the creature is displaced from the original position to the one leg side which is in the standing-leg state and in the stretching motion. As a result, the bending motion of the other leg can be facilitated. The original position of the center of gravity means a position of the center of gravity in a state the creature is standing and still with the pair of right and left legs lined together in the front-back direction.

On the other hand, in the fourth designated period subsequent to the third designated period, the center of gravity of the creature is displaced to the side of the other leg in the lifted-leg state in the bending motion, that is, towards the original position. As a result, the displacement amount of the center of gravity of the creature is restricted, and it is able to avoid a situation in which the posture thereof becomes unstable.

Therefore, by controlling the operation of each of the pair of actuators so as to adjust the length of each of the third designated period and the fourth designated period, the swinging range of the center of gravity of the creature in the right-left direction is appropriately restricted from the view point of stabilizing the posture, and the walking motion thereof is smoothened. As the control method, a feed back control is adopted. For example, the result of multiplying an appropriate gain coefficient to the deviation amount of the swinging range of the center of gravity of the creature in the right-left direction from the permissible range, may be added or subtracted to one or both of an amplitude and phase of the motive power of the actuator.

It is preferable that the controller is configured to control the temporal change manner of the motive power of the actuators so that each of the third designated period and the fourth designated period becomes a different length, in a case where the one leg is the right leg and the other leg is the left leg, and in a case where the one leg is the left leg and the other leg is the right leg.

According to the walking motion assist device of the above configuration, the symmetry or the asymmetry of the swinging manner of the center of gravity of the creature in the right-left direction can be controlled. For example, even in a case where the exercise ability of the pair of right and left legs differ, the swinging manner of the center of gravity of the creature in the right and left direction can be controlled symmetrically. Therefore, the walking motion can be smoothened while achieving stability of the posture of the creature.

It is preferable that the controller is configured to control the temporal change manner of the motive power of the actuators so that the assisting force or a work in a standing-leg period of the leg indicates a greatest value or a maximum value in the third designated period.

According to the walking motion assist device of the second aspect of the present invention, in the third designated period (prior period in the standing-leg period) of one leg among the pair of right and left legs of the creature, the translation of the body derived from the floor reaction force acting on the one leg is more prompted compared to other periods in the standing-leg period. The third designated period of the one leg overlaps a period immediately after the other leg transits from the standing-leg period to the lifted-leg period. Therefore, smooth bending motion of the other leg is facilitated so as to follow the translation of the body.

It is preferable that the controller is configured to control the temporal change manner of the motive power of the actuators so that the assisting force or the work in the standing-leg period of the leg converges or approaches asymptotically to zero in the fourth designated period.

According to the walking motion assist device of the above configuration, in a middle period or the later period of the standing-leg period of one leg, the one leg becomes in a state capable of moving without being restricted by the operation of the actuator. Therefore, in the third designated period of the other leg, smooth bending motion of the one leg is facilitated so as to follow the translation of the body being relatively largely facilitated as described above.

It is preferable that the controller is configured to adjust the greatest value or the maximum value of the assisting force or a work in the third designated period so that an overlapping period of a standing-leg period of each of the pair of right and left legs of the creature approaches zero.

According to the walking motion assist device of the above configuration, it is able to uniformly shorten a both-legs-supported period in which both of the legs are in the standing-leg state, even if the followability of the floor leaving motion of the leg associated with the translation of the body is right-left asymmetry or different due to the individual difference of the creature and the like. Therefore, in the standing-leg period of one leg, it is able to avoid a situation in which the other leg is dragged due to delay of floor leaving of the other leg.

It is preferable that the controller is configured to control the temporal change manner of the motive power of the actuators so that the assisting force or a work in a lifted-leg period of the leg indicates a greatest value or a maximum value in a fifth designated period which is a period from a transition of the leg to a stretching motion state from a bending motion state, until it becomes the standing-leg state.

According to the walking motion assist device of the above configuration, in the fifth designated period of one leg, the translation of the body derived from the floor reaction force acting on the one leg is more prompted compared to other periods of the lifted-leg period. By doing so, the floor reaction force acting on the one leg immediately after the start of the third designated period continuing from the fifth designated period of the one leg, is increased. Therefore, the translation of the body as above in the third designated period is further largely facilitated, and smooth bending motion of the other leg is further facilitated.

DESCRIPTION OF THE PREFERRED EMBODIMENTS

Construction

Figure 1:
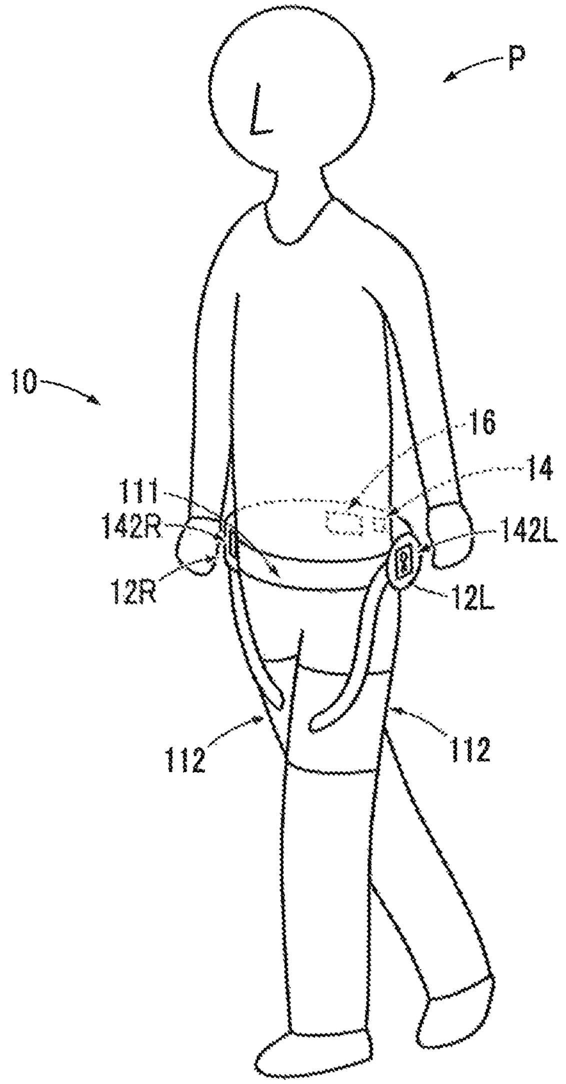
FIG. 1 is an explanatory diagram illustrating the construction of a walking motion assist device as one embodiment of the present invention.

A walking motion assist device 10 illustrated in FIG. 1 as one embodiment of the present invention is equipped with a first attachment 111 attached to a body of a human P as the creature, a second attachment 112 attached to each leg of the human P, an actuator 12, a controller 14 configured to control an operation of the actuator 12, a hip joint angle sensor 142, and a battery 16.

The walking motion assist device 10 has substantially the same configuration with the device described in Japanese Patent No. 4271713 except for the features of the controller 14. Therefore, the explanation related to the same features is abbreviated. The walking motion assist device 10 is configured to assist the walking motion of the human P by acting a motive power of the actuator 12 having the battery 16 as a power source on the human P.

Figure 2:
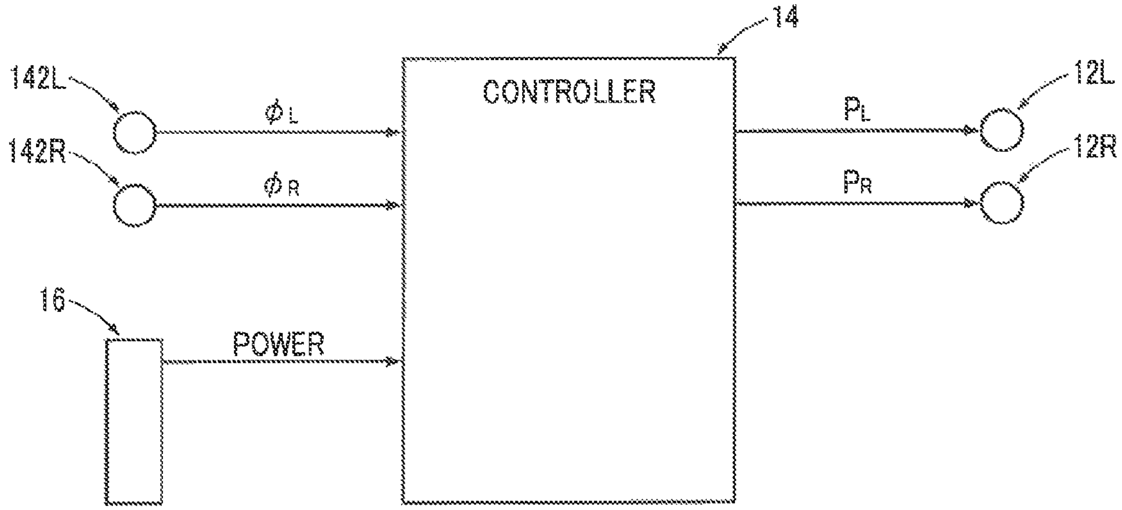
FIG. 2 is an explanatory diagram of a configuration of a controller.

The controller 14 shown in FIG. 2 is constituted of a computer and is configured to execute control processing of the operation of the actuator, and thus the assisting force acted on the human P. The controller 14 is configured to execute predetermined arithmetic processing means that an arithmetic processing unit (CPU) constituting the controller 14, reads necessary data and application software from a storage device (memory) and is programmed to execute the predetermined arithmetic processing according to the software.

Reference characters “R” and “L” will be used to distinguish the right and the left of legs and the like, but the reference characters will be omitted in the case where there is no need to distinguish between the right and the left or in the case where vectors having right and left components are expressed. Further, signs “+” and “−” will be used to distinguish between a bending motion (a forward motion) and a stretching motion (a backward motion) of the legs (specifically, a thigh portion).

In a case where the creature is a quadrupedal, the motion assist method of the right and left legs of the human P can be applied to one or both of right and left forelegs and right and left back legs.

Function

First Embodiment

Figure 3:
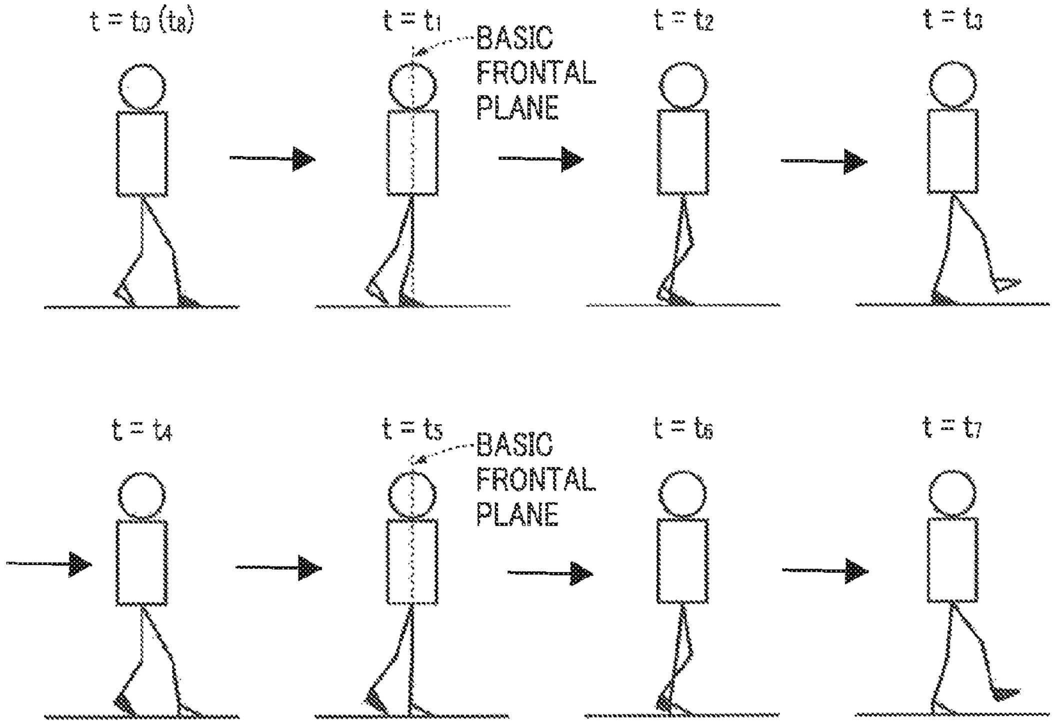
FIG. 3 is an explanatory diagram regarding a first transition manner of a walking motion state.

When a human P performs walking motion in a state wearing the walking motion assist device 10, a walking motion state of the human P in each walking motion cycle transits as illustrated in FIG. 3.

More specifically, when t=t0, the right leg (black) transits from a lifted-leg state to a standing-leg state. At t=t1, the right leg in the standing-leg state performs stretching motion, and thereby its posture matches a basic frontal plane (dashed line). At t=t2, the right leg in the standing-leg state further performs stretching motion, and thereby its posture changes to a rear side of the basic frontal plane. At t=t3, the left leg (white) terminates the bending motion in the lifted-leg state. At t=t4, the left leg in the lifted-leg state performs stretching motion while transiting to the standing-leg state. At t=t5, the left leg in the standing-leg state performs stretching motion, and thereby its posture matches the basic frontal plane (dashed line). At t=t6, the left leg in the standing-leg state further performs stretching motion, and thereby its posture changes to the rear side of the basic frontal plane. Then, at t=t7, the right leg in the lifted-leg state terminates the bending motion. Thereafter, at t=t8, the same state as t=t0 is replicated.

The periods t=t0 to t4 correspond to the “standing-leg period” and other periods correspond to the “lifted-leg period”. The prior periods t=t0 to t1 in the standing-leg period correspond to a “first designated period”, and the later periods t=t7 to t8 in the lifted-leg period correspond to a “second designated period”.

Signals expressing corresponding hip joint angle $\phi$ are output from the hip joint angle sensor 142, and input to the controller 14. The hip joint angle $\phi$ is defined as an angle formed by a straight line segment expressing the basic frontal plane and a straight line segment expressing the thigh portion when the human P is seen from a normal line direction of a sagittal plane. The hip joint angle $\phi$ is defined as positive (+) in a case where the thigh portion is in the forward side of the basic frontal plane, while defined as negative (−) in a case where the thigh portion is in the rear side of the basic frontal plane. Right hip joint angle $\phi_R(t)$ temporally changes, for example, as shown by the solid line in FIG. 4.

Each of the plurality of time points t0 to t7 in the abscissa axis, correspond to each of the walking motion state indicated in FIG. 3. The mutual time interval between each time point t=t0 to t7 may differ from the illustrated reduction scale.

The controller 14 sets the assisting force $T(t)=f(\phi(t))$ according to a predetermined algorithm f based on the hip joint angle $\phi(t)$, and controls the power supply $E(t)=g(T(t))$ with respect to the actuator 12 from the battery 16 according to the assisting force T(t). The predetermined algorithm is defined by a calculation formula or a table and the like in which the assisting force $T_k=f(\phi_k)$ is unambiguously determined based on the hip joint angle $\phi_k$, and is stored in the storage device configuring the controller 14. The assisting force T is set in flux, for example, as indicated by the one-dot chain line or the two-dot chain line in FIG. 4. The algorithm f may adopt, for example, an algorithm having an oscillator as the basis for generating the assisting force T as described in Patent Document 1.

Based on the temporal change manner of the hip joint angle $\phi(t)$, the controller 14 determines the distinction between the bending motion state and stretching motion state, and the distinction between the standing-leg state and the lifted-leg state of each leg. The distinction of the standing-leg state and the lifted-leg state of each leg may be determined by providing a contact sensor at each sole of the foot and basing on the signals output from the contact sensor according to contact or non-contact between the foot sole and the floor. The distinction of the standing-leg state and the lifted-leg state of each leg may be determined by providing an acceleration sensor to the first attachment 111 and basing on the temporal change manner of the signals output from the acceleration sensor according to the acceleration in the vertical direction of the human P.

More specifically, the assisting force $T_R$ of the right leg in the standing-leg period t=t0~t4 is controlled to indicate a greatest value or a maximum value in the first designated period t=t0 to t1 which is a period from the start of stretching motion of the right leg until its posture matches the posture of the basic frontal plane (refer to the one-dot chain line and the two-dot chain line). For example, from the view point of smoothening or speeding up the walking motion of human, the assisting force $T_R$ may be controlled so as to indicate the greatest value or the maximum value in the initial period or the prior periods t=t0+0.2(t1−t0)~t0+0.5(t1−t0) among the first designated period.

After the assisting force $T_R$ of the right leg in the standing-leg period t=t0 to t4 indicates the greatest value or the maximum value in the first designated period t=t0 to t1, the assisting force $T_R$ in the period until the standing-leg period terminates t=t3 to t4, converges or approaches asymptotically to zero, and then maintained to zero (refer to the one-dot chain line and the two-dot chain line).

The assisting force $T_R$ of the right leg in the lifted-leg period t=t4 to t8 is controlled so as to indicate the greatest value or the maximum value in the second designated period t=t7 to t8, which is a period in which the right leg transits from the bending motion state to the stretching motion state and then to the standing-leg state (refer to the one-dot chain line). As another embodiment, the assisting force $T_R$ of the right leg in the lifted-leg period t=t4 to t8 is controlled so as to gradually increase in the second designated period t=t7 to t8 (refer to the two-dot chain line).

The assisting force $T_L(t)$ of the left leg is controlled similarly to the assisting force $T_R(t)$ of the right leg. Here, the greatest value or the maximum value of one or both of the assisting force $T_L(t)$ and $T_R(t)$ in the first designated period is adjusted so that the overlapping period of the standing-leg period of each of the right and left leg approaches to zero.

In place of assisting force T, a work (a product of the assisting force (torque) and the variation amount of the hip joint angle) may be controlled so as to temporally change according to the above described manner.

Effect

First Embodiment

Figure 4:
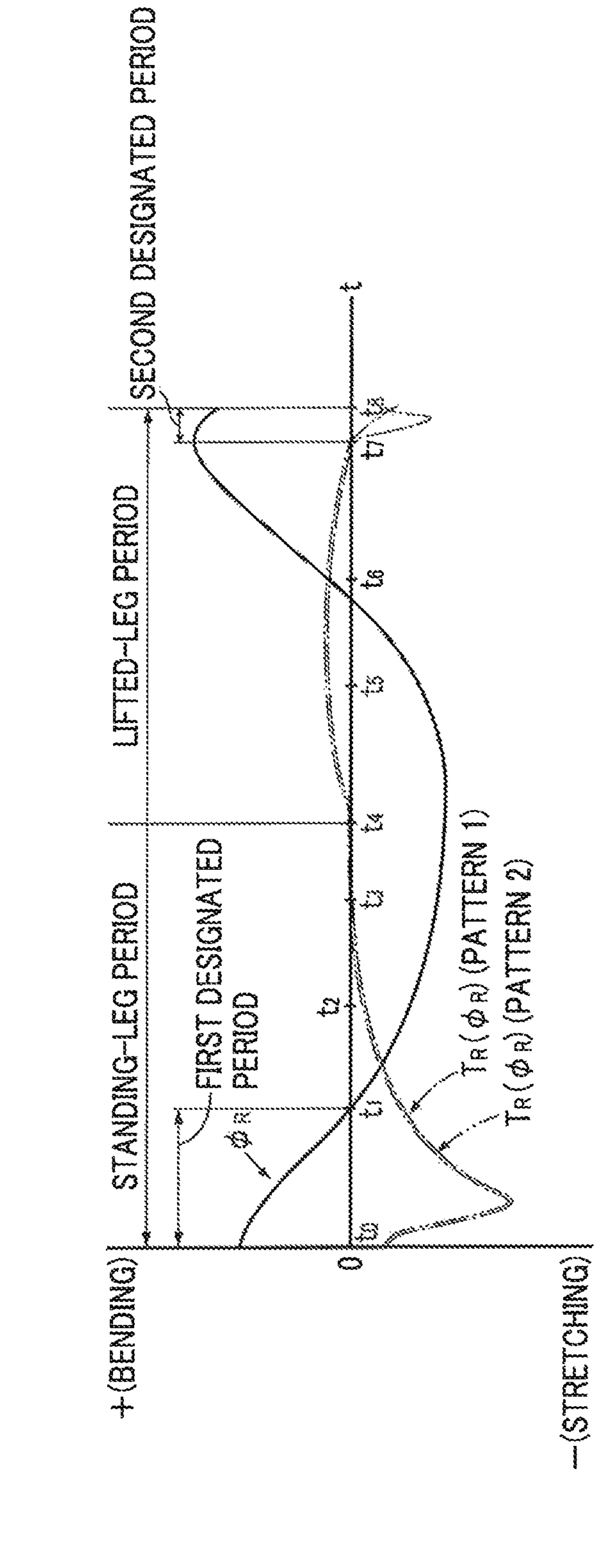
FIG. 4 is an explanatory diagram regarding a first temporal change manner of an assisting force.

The assisting force T in the standing-leg period of the leg is controlled so as to indicate the greatest value or the maximum value in the "first designated period" (refer to the one-dot chain line and the two-dot chain line in t=t0 to t1 of FIG. 4). By doing so, in the first designated period of one leg (initial period or prior period of the standing-leg period), the translation of the body derived from the floor reaction force acting on the one leg is induced larger compared to other periods in the standing-leg period. Since the first designated period of the one leg overlaps at least one of the periods immediately before or immediately after the time point when the other leg transits from the standing-leg state to the lifted-leg state, start of smooth floor leaving or bending motion of the other leg is prompted so as to follow the translation of the body.

After the assisting force T in the standing-leg period of the leg indicates the greatest value or the maximum value in the "first designated period", it is maintained to zero until the standing-leg period terminates (refer to the one-dot chain line and the two-dot chain line of t=t3 to t4 in FIG. 4). By doing so, in the later period of the standing-leg period of one leg, that is, immediately before or immediately after the start of the standing-leg period of the other leg, the one leg becomes in a state capable of moving without being restricted by the operation of the actuator 12. Therefore, in the first designated period of the other leg, following the translation of the body being relatively largely facilitated as described above, smooth start of floor leaving and bending motion of the one leg is prompted.

The assisting force of the leg in the lifted-leg period is controlled so as to indicate the greatest value or the maximum value in the "second designated period" (refer to the one-dot chain line of t=t7 to t8 in FIG. 4). By doing so, in the second designated period of one leg, the translation of the body derived from the floor reaction force acting on the one leg is largely prompted compared to other periods in the lifted-leg period. By doing so, the floor reaction force acting on the one leg is increased immediately after the start of the first designated period continuing from the second designated period of the one leg. Therefore, the translation of the body as described above in the first designated period is further more facilitated, and smooth start of floor leaving and bending motion of the other leg is further facilitated.

The greatest value or the maximum value of the assisting force in the first designated period is adjusted so that the overlapping period of the standing-leg period of each leg approaches zero. By doing so, it is able to uniformly shorten a both-legs-supported period in which both of the legs are in a standing-leg state, even if the followability of the floor leaving motion of the leg associated with the translation of the body is right-left asymmetry or different due to an individual difference of the creature. Therefore, in the first designated period of one leg, a situation in which the other leg is dragged due to delay of floor leaving of the other leg is avoided.

Experiment Result

First Embodiment

In each of FIG. 5 to FIG. 8, experiment results 1 to 4 related to the temporal change manner of the hip joint angle φ(t) and the assisting force T(t) are indicated, respectively. Each of the experiment results 1 to 4 was obtained under the condition that each of (1) desired phase difference $\delta_L$ between the assisting force $T_L$ of the left leg and the left hip joint angle $\phi_L$, (2) desired phase difference $\delta_R$ between the assisting force $T_R$ of the right leg and the right hip joint angle $\phi_R$, and (3) the maximum value Tmax—of the stretching side assisting force T, was controlled as shown in Table 1.

The phase difference δ between the assisting force T and the hip joint angle φ is defined, for example, as a result of converting the difference between the time point when the assisting force T indicates the maximum value at the stretching side (or the bending side) and the time point when the hip joint angle φ indicates the maximum value at the stretching side (or the bending side), or the average value of the difference, with reference to a phase variation amount 2π [rad] across a walking motion cycle S of the human P. The phase difference δ is defined as a positive value (+) in a case where the assisting force T is leading in phase than the hip joint angle φ, while defined as a negative value (−) in a case the assisting force T is delayed in phase than the hip joint angle φ. Table 1 also shows a measurement result of the walking cycle S of the human P.

TABLE 1

| Experiment | Left desired phase difference $\delta_L$ [rad] | Right desired phase difference $\delta_R$ [rad] | Maximum value Tmax-[Nm] | Walking motion cycle S[s] |
|---|---|---|---|---|
| 1 | 0 | 0 | 4.2 | 39.69 |
| 2 | −0.5 | −0.5 | 3.0 | 38.46 |
| 3 | −1.0 | −1.0 | 3.0 | 37.10 |
| 4 | +0.5 | +0.5 | 3.0 | 51.18 |

Figure 5:
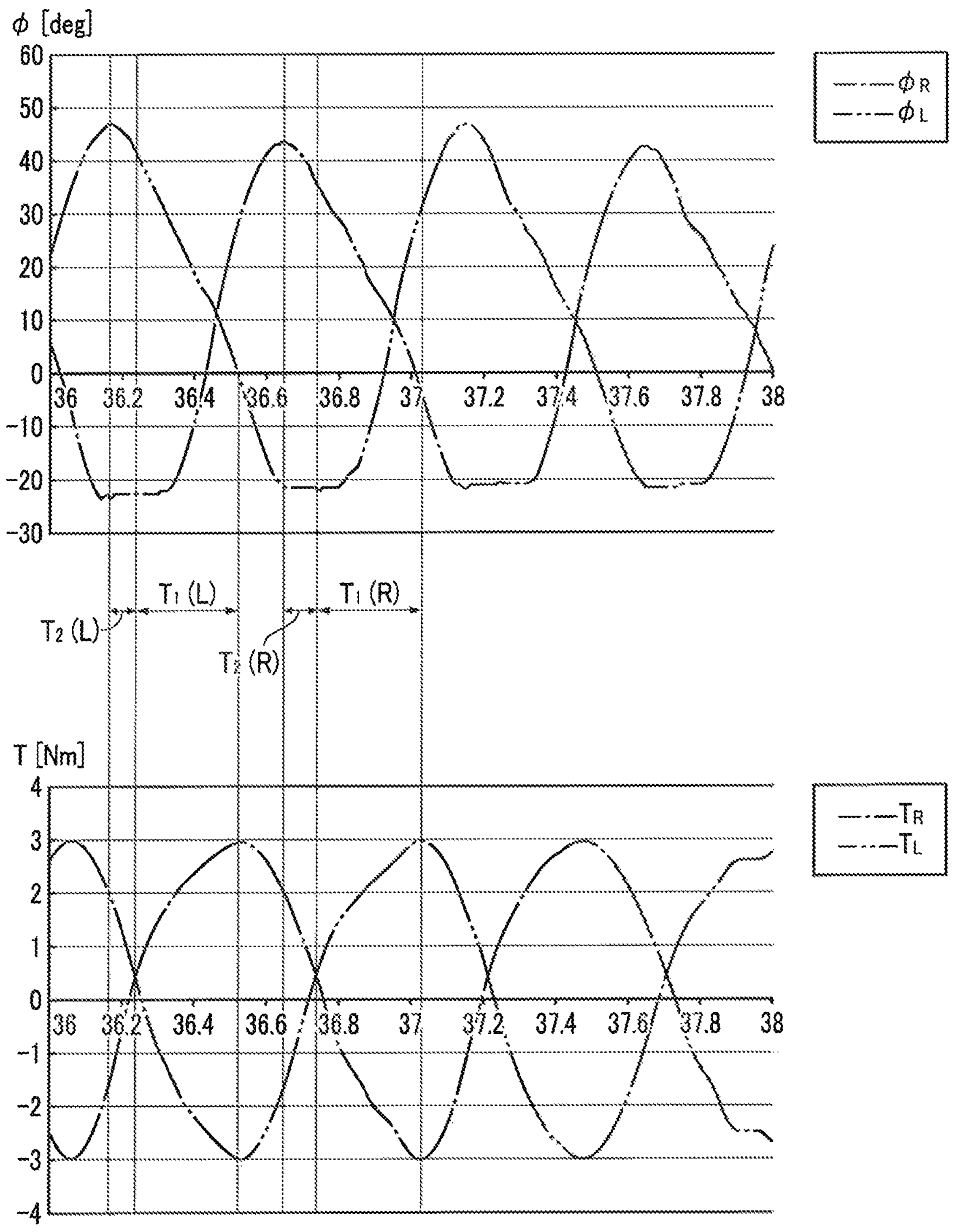
FIG. 5 is an explanatory diagram related to experiment result 1 (example 1)

In experiment 1 (example 1), the assisting force T was controlled such that the assisting force $T_L(t)$ of the left leg indicated a maximum value in the later period (or the terminal period) of the first designated period T1(L) of the left leg, and the assisting force $T_R(t)$ of the right leg indicated a maximum value in the later period of the first designated period T1(R) of the right leg (refer to FIG. 5). The walking motion cycle S in this case was 39.69 [s], and the test subject (human P) is able to walk with a sense similar to usual by receiving motion assist by the walking motion assist device 10 (refer to Table 1).

Figure 6:
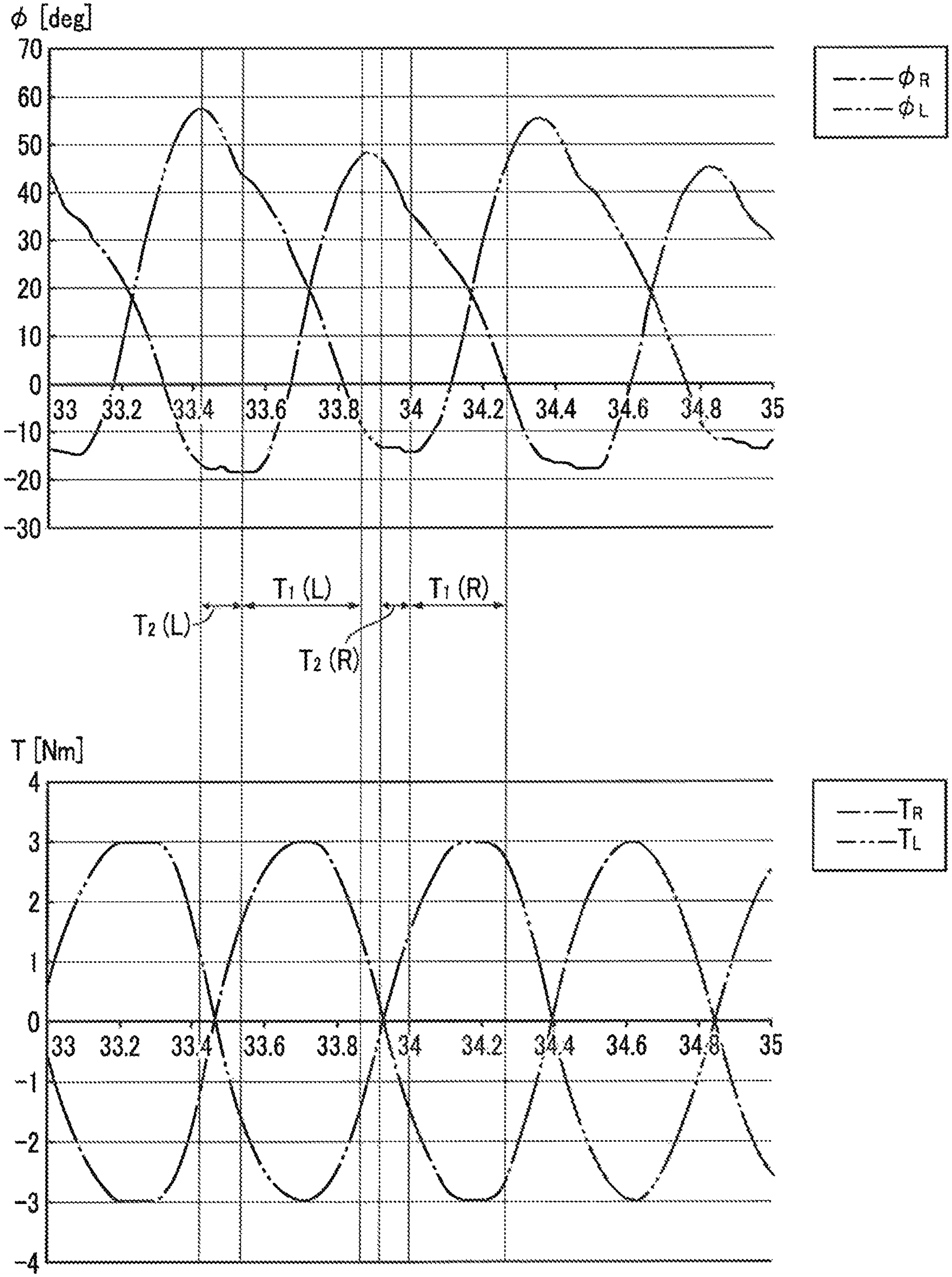
FIG. 6 is an explanatory diagram related to experiment result 2 (example 2)

In experiment 2 (example 2), the assisting force T was controlled such that the assisting force $T_L(t)$ of the left leg indicated a maximum value in the middle period of the first designated period T1(L) of the left leg, and the assisting force $T_R(t)$ of the right leg indicated a maximum value in the middle period of the first designated period T1(R) of the right leg (refer to FIG. 6). The walking motion cycle S in this case was 38.46 [s], and the test subject is able to walk by realizing that the moving speed is faster than usual by receiving motion assist by the walking motion assist device 10 (refer to Table 1).

Figure 7:
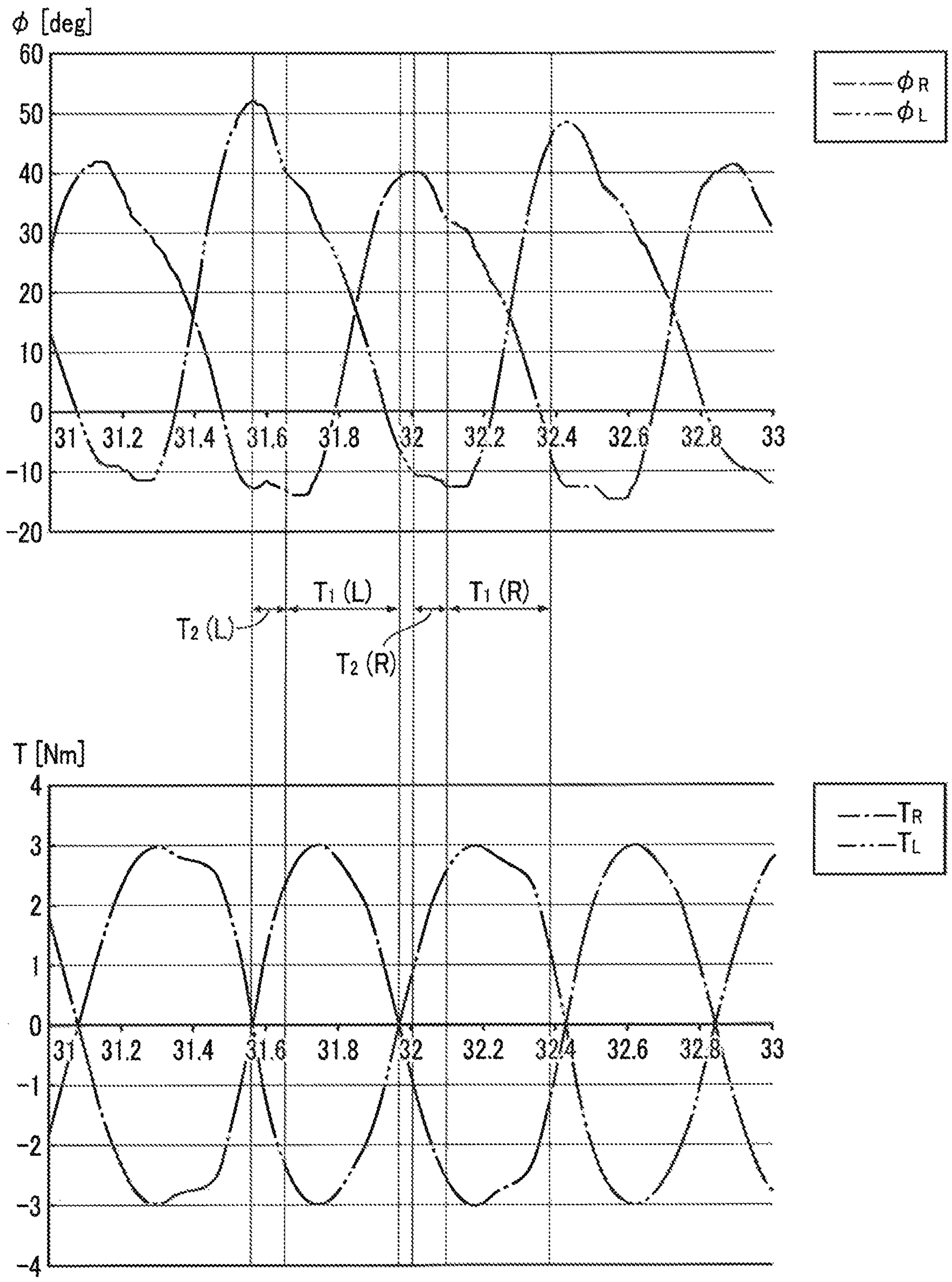
FIG. 7 is an explanatory diagram related to experiment result 3 (example 3)

In experiment 3 (example 3), the assisting force T was controlled such that the assisting force $T_L(t)$ of the left leg indicated a maximum value in the prior period (or the initial period) of the first designated period T1(L) of the left leg, and the assisting force $T_R(t)$ of the right leg indicated a maximum value in the prior period of the first designated period T1(R) of the right leg (refer to FIG. 7). The walking motion cycle S in this case was 38.46 [s], and the test subject is able to walk by realizing that the moving speed is further faster by receiving motion assist by the walking motion assist device 10 (refer to Table 1).

Figure 8:
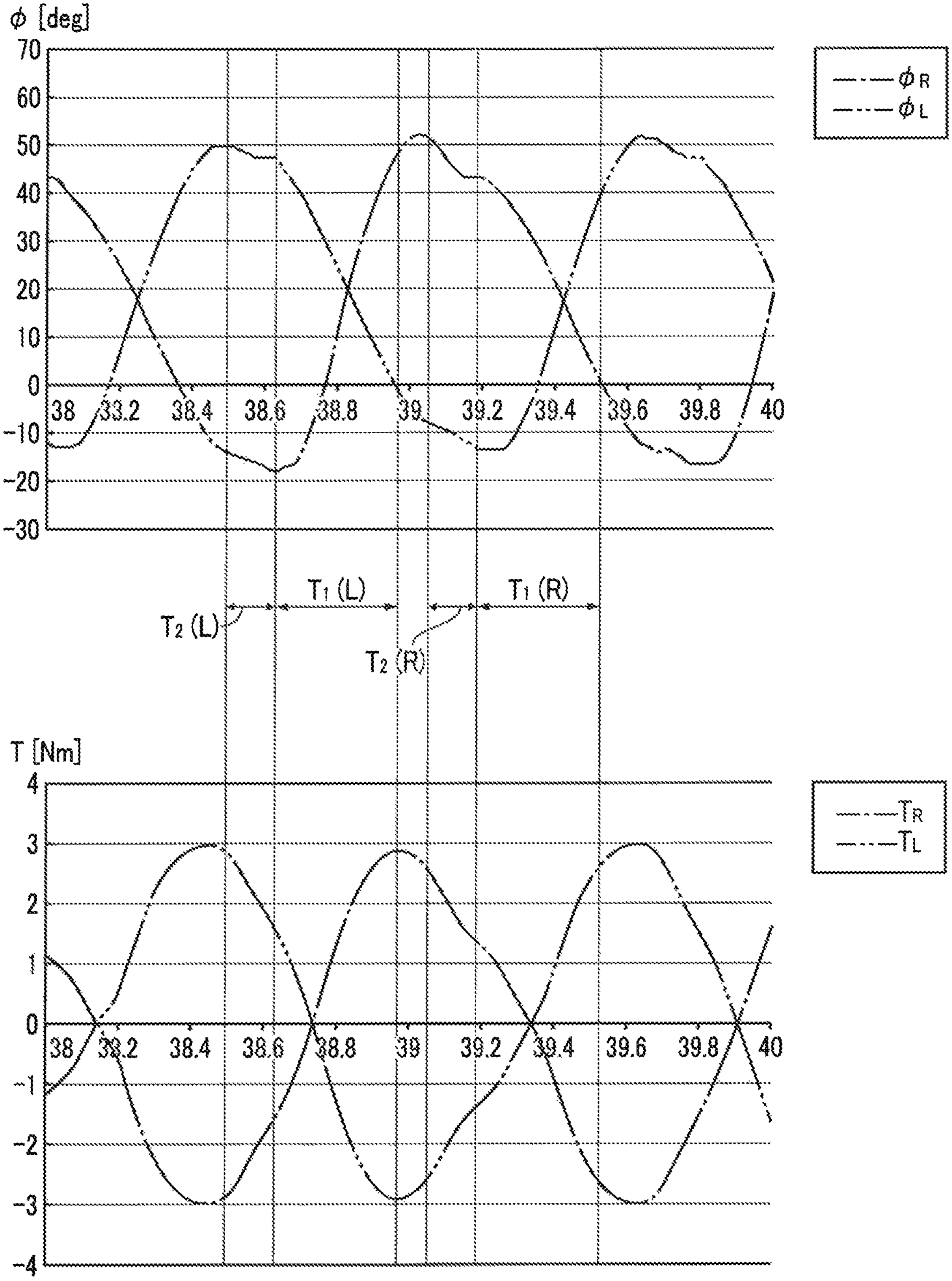
FIG. 8 is an explanatory diagram related to experiment result 4 (comparative example)

In experiment 4 (comparative example 4), the assisting force T was controlled such that the assisting force $T_L(t)$ of the left leg indicated a maximum value after the first designated period T1(L) of the left leg elapsed, and the assisting force $T_R(t)$ of the right leg indicated a maximum value after the first designated period T1(R) of the right leg elapsed (refer to FIG. 8). The walking motion cycle S in this case was 51.18 [s], and the test subject walks by realizing that the moving speed is slower than usual while receiving motion assist by the walking motion assist device 10 (refer to Table 1).

Function

Second Embodiment

Figure 9:
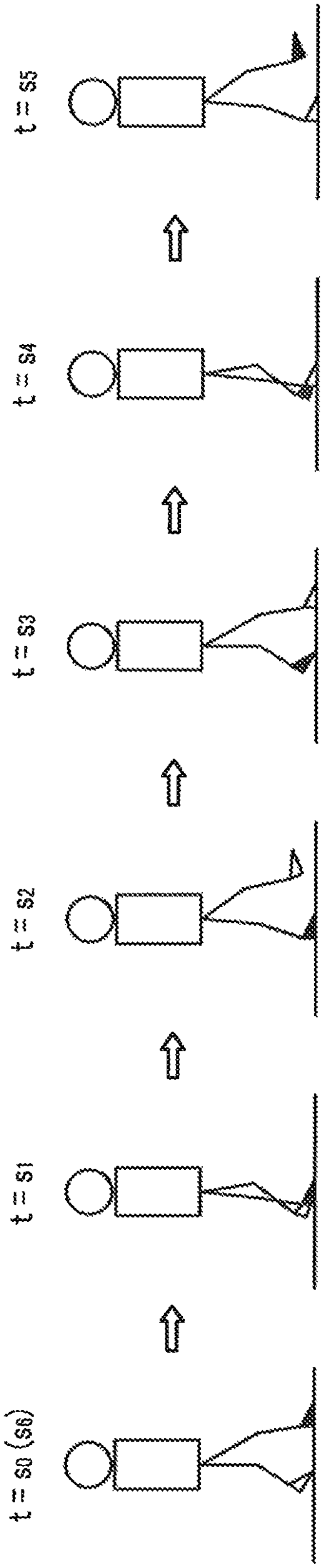
FIG. 9 is an explanatory diagram regarding a second transition manner of the walking motion state.

When a human P performs walking motion in a state wearing the walking motion assist device 10, a walking motion state of the human P in each walking motion cycle transits as illustrated in FIG. 9.

More specifically, when t=s0, the right leg (black) transits from a lifted-leg state to a standing-leg state. At t=s1, the posture of the right leg performing stretching motion in the standing-leg state changes to a rear side of the basic frontal plane. At t=s2, the left leg (white) terminates the bending motion in the lifted-leg state. At t=s3, the left leg performs stretching motion in the lifted-leg state while transiting to the standing-leg state. At t=s4, the posture of the left leg performing stretching motion in the standing-leg state, changes to the rear side of the basic frontal plane. Then, at t=s5, the right leg terminates the bending motion in the lifted-leg state. Thereafter, at t=s6, the same state as t=s0 is replicated.

Figure 10:
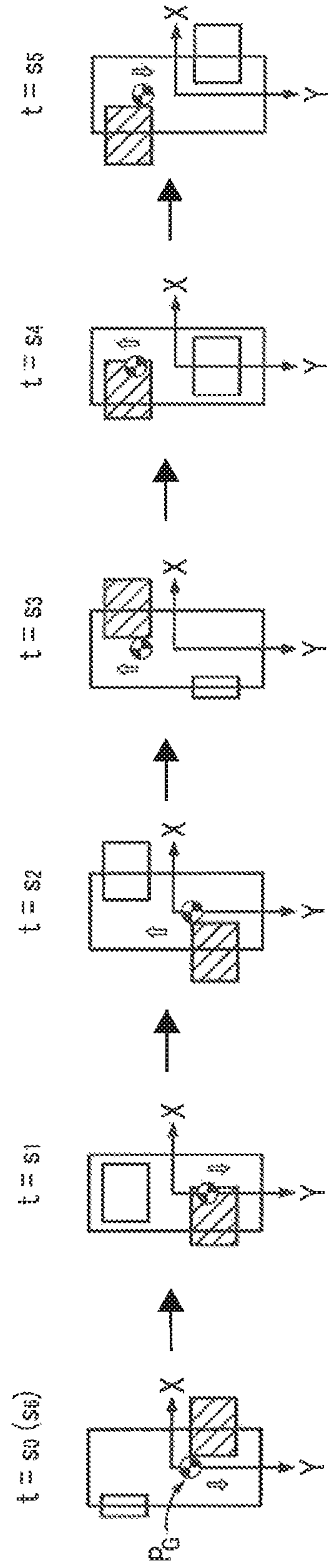
FIG. 10 is an explanatory diagram regarding a temporal change manner of a center of gravity position.

As shown in FIG. 10, the center of gravity $P_G$ of the human P in walking motion so as to translate forward (+X direction) swings to the right and left direction (±Y direction).

The periods t=s0 to s3 correspond to a "standing-leg period" of the right leg and a "lifted-leg period" of the left leg, other periods s3 to s6 correspond to the "lifted-leg period" of the right leg and the "standing-leg period" of the left leg. Regarding the right leg, the prior periods t=s0 to s1 in the standing-leg period correspond to a "third designated period", the middle periods t=s1 to s2 in the standing-leg period correspond to a "fourth period", and the later periods t=s5 to s6 in the lifted-leg period correspond to a "fifth designated period". Regarding the left leg, the prior periods t=s3 to s4 in the standing-leg period correspond to the "third designated period", the middle periods t=s4 to s5 in the standing-leg period correspond to the "fourth period", and the later periods t=s2 to s3 in the lifted-leg period correspond to the "fifth designated period".

Signals expressing corresponding hip joint angle $\phi$ are output from the hip joint angle sensor 142, and input to the controller 14. The hip joint angle $\phi$ is defined as an angle formed by a straight line segment expressing the basic frontal plane and a straight line segment expressing the thigh portion when the human P is seen from a normal line direction of a sagittal plane. The hip joint angle $\phi$ is defined as positive (+) in a case where the thigh portion is in the forward side of the basic frontal plane, while defined as negative (−) in a case where the thigh portion is in the rear side of the basic frontal plane. Right hip joint angle $\phi_R(t)$ temporally changes, for example, as shown by the solid line in FIG. 11.

Figure 11:
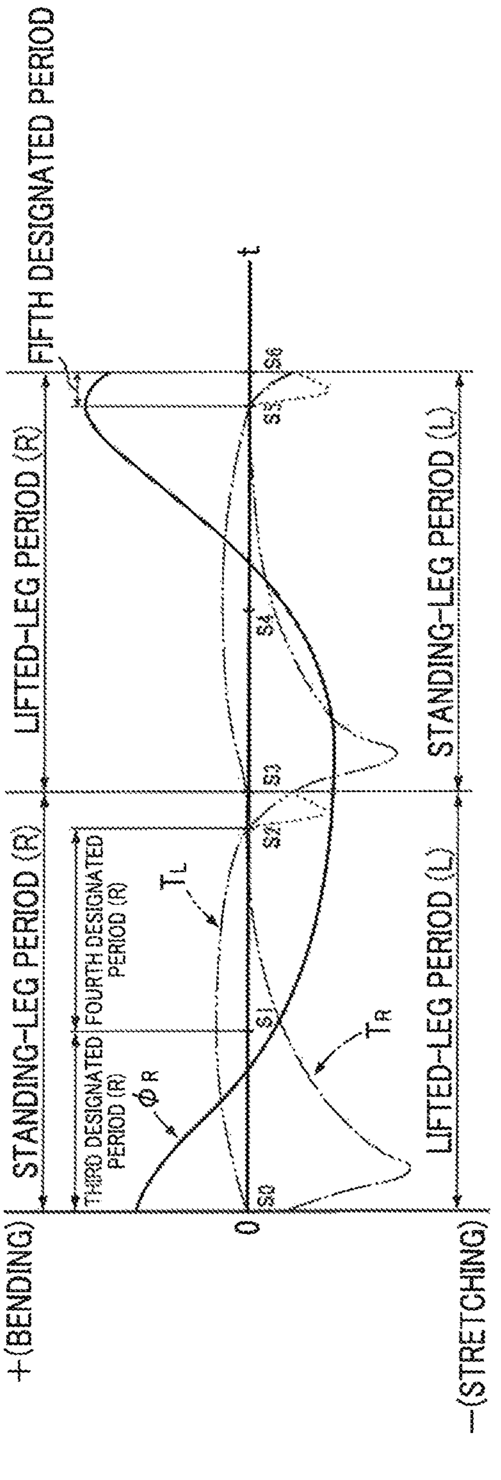
FIG. 11 is an explanatory diagram regarding a second temporal change manner of the assisting force.
Figure 12A:
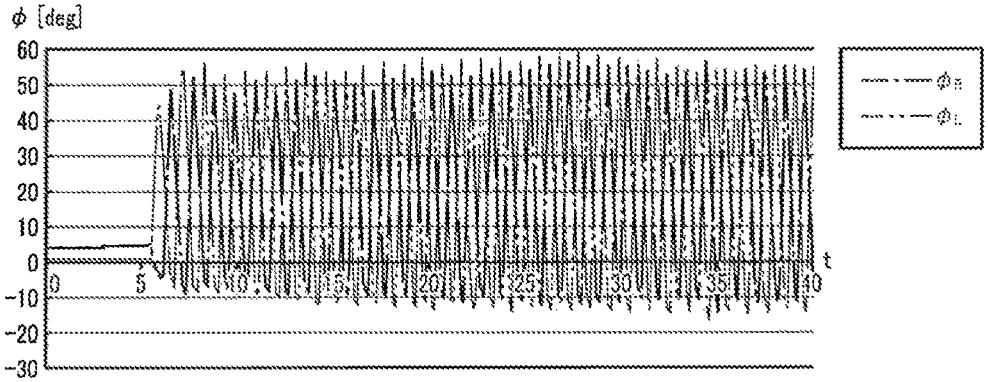
FIG. 12A, FIG. 12B, FIG. 12C, and FIG. 12D are explanatory diagrams related to temporal change manner of a hip joint angle of examples 1 to 4.
Figure 12B:
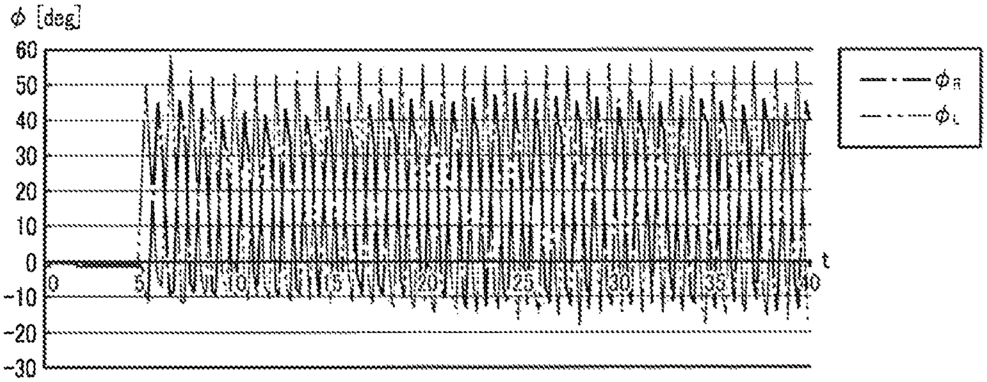
Figure 12C:
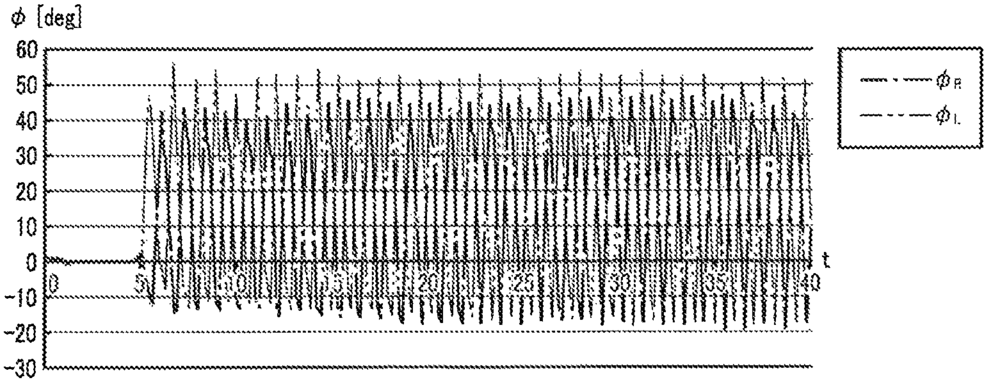
Figure 12D:
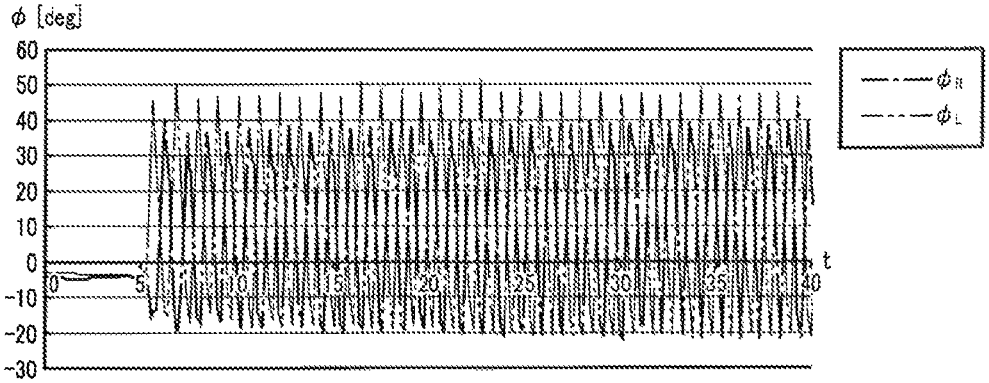
Figure 13A:
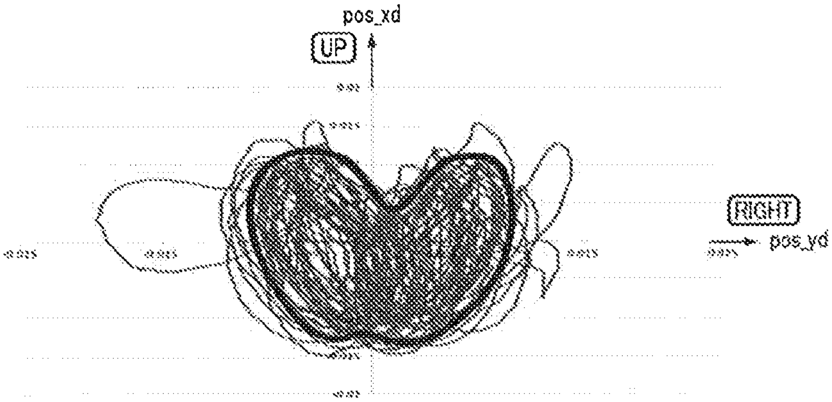
FIG. 13A, FIG. 13B, FIG. 13C, and FIG. 13D are explanatory diagrams related to a center of gravity position trajectory of examples 1 to 4.
Figure 13B:
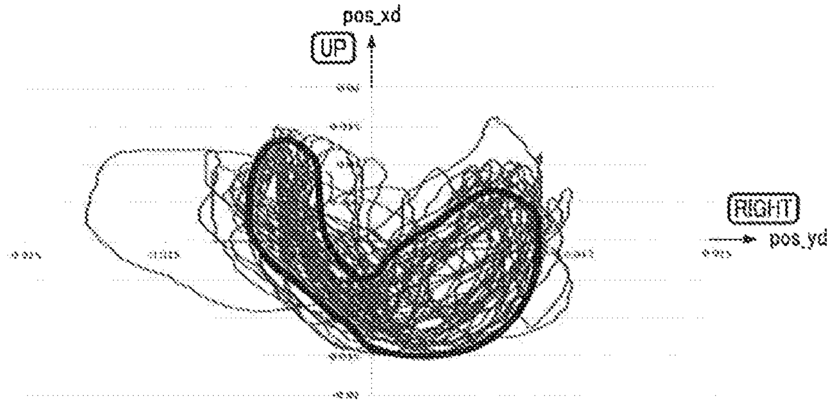
Figure 13C:
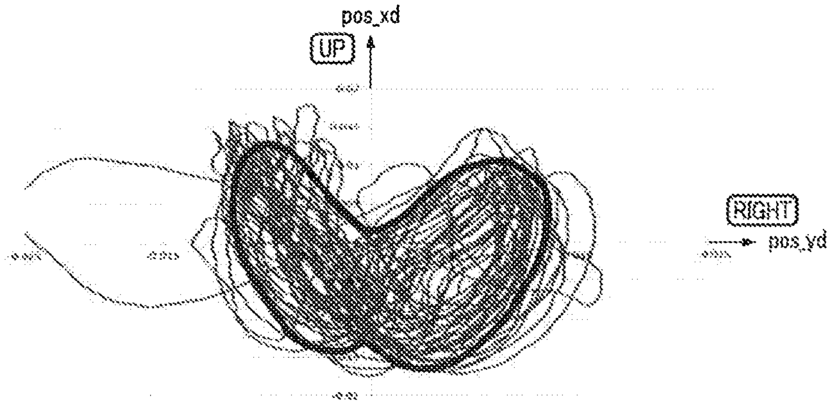
Figure 13D:
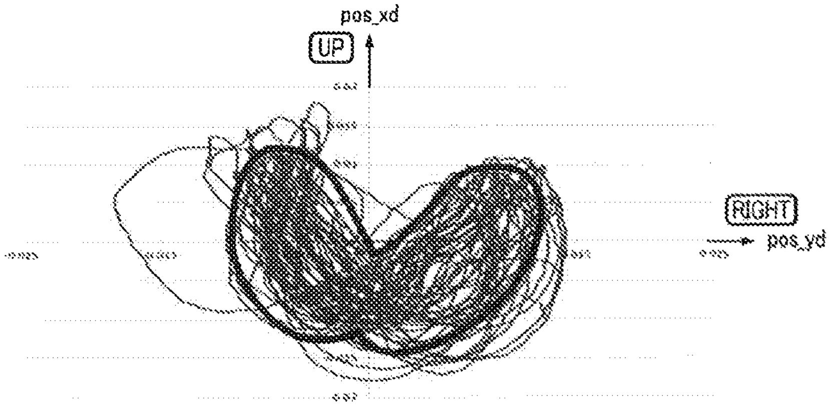

Each of the plurality of time points s0 to s6 in the abscissa axis shown in FIG. 11, corresponds to each of the walking motion state indicated in FIG. 9 and FIG. 10. The mutual time interval between each time point t=s0 to s6 may differ from the illustrated reduction scale.

The controller 14 sets the assisting force $T(t)=f(\phi(t))$ according to a predetermined algorithm f based on the hip joint angle $\phi(t)$, and controls the power supply $E(t)=g(T(t))$ with respect to the actuator 12 from the battery 16 according to the assisting force $T(t)$. The assisting force $T_R$ of the right leg and the assisting force $T_L$ of the left leg are set in flux, for example, as indicated by each of the one-dot chain line and the two-dot chain line in FIG. 11. The predetermined algorithm is defined by a calculation formula or a table and the like in which the assisting force $T_k=f(\phi_k)$ is unambiguously determined based on the hip joint angle $\phi_k$, and is stored in the storage device configuring the controller 14. The algorithm f may adopt, for example, an algorithm having an oscillator as the basis for generating the assisting force T as described in Patent Document 1.

Based on the temporal change manner of the hip joint angle $\phi(t)$, the controller 14 determines the distinction between the bending motion state and the stretching motion state, and the distinction between the standing-leg state and the lifted-leg state of each leg. The distinction of the standing-leg state and the lifted-leg state of each leg may be determined by providing a contact sensor at each sole of the foot and basing on the signals output from the contact sensor according to contact or non-contact between the foot sole and the floor. The distinction of the standing-leg state and the lifted-leg state of each leg may be determined by providing an acceleration sensor to the first attachment 111 and basing on the temporal change manner of the signals output from the acceleration sensor according to the acceleration in the vertical direction of the human P.

More specifically, the assisting force $T_R$ is acted on the stretching direction of the right leg in the standing-leg state and the assisting force $T_L$ is acted on the bending direction of the left leg in the lifted-leg state (refer to t=s0 to s2). In such case, the length (long/short) of each of the third designated period t=s0 to s1 and the successive fourth designated period t=s1 to s2 is adjusted. For example, it is set to $|s1-s0|=\alpha|s2-s0|$ and $|s2-s1|=(1-\alpha)|s2-s0|$ $(0<\alpha<0.5)$.

The third designated period t=s0 to s1 in a case where the right leg is in a standing-leg state and the left leg is in the lifted-leg state, is a period in which a state that the stretching assisting force $T_R$ acting on the right leg being stronger than the bending assisting force $T_L$ acting on the left leg, is continued. In such case, the fourth designated period t=s1 to s2 is a period in which a state that the bending assisting force $T_L$ acting on the left leg being stronger than the stretching assisting force $T_R$ acting on the right leg, is continued.

Similarly, the assisting force $T_R$ is acted on the bending direction of the right leg in the lifted-leg state and the assisting force $T_L$ is acted on the stretching direction of the left leg in the standing-leg state (refer to t=s3 to s5). In such case, the length (long/short) of each of the third designated period t=s3 to s4 and the successive fourth designated period t=s4 to s5 is adjusted. For example, it is set to $|s4-s3|=\beta|s5-s3|$ and $|s5-s4|=(1-\beta)|s5-s3|(0<\beta<0.5)$.

The third designated period t=s3 to s4 in a case where the left leg is in the standing-leg state and the right leg is in the lifted-leg state, is a period in which a state that the stretching assisting force $T_L$ acting on the left leg being stronger than the bending assisting force $T_R$ acting on the right leg, is continued. In such case, the fourth designated period t=s4 to s5 is a period in which a state that the bending assisting force $T_R$ acting on the right leg being stronger than the stretching assisting force $T_L$ acting on the left leg, is continued.

The values of $\alpha$ and $\beta$ may be the same or may be different. By distinguishing the values of $\alpha$ and $\beta$, the temporal change manner of the motive power of the actuator 12 is controlled such that each of the third designated period and the fourth designated period becomes a different length between the cases where the right leg is in the standing-leg state and the left leg is in the standing-leg state.

The temporal change manner of the motive power of the actuator 12R is controlled such that the assisting force $T_R$ of the right leg in the standing-leg period t=s0 to s3 indicates the greatest value or the maximum value in the third designated period t=s0 to s1. The temporal change manner of the motive power of the actuator 12L is controlled such that the assisting force $T_L$ of the left leg in the standing-leg period t=s3 to s6 indicates the greatest value or the maximum value in the third designated period t=s3 to s4.

The temporal change manner of the motive power of the actuator 12L is controlled such that the assisting force of the right leg in the standing-leg period t=s0 to s3 converges or approaches asymptotically to zero in the fourth designated period t=s1 to s2. The temporal change manner of the motive power of the actuator 12R is controlled such that the assisting force of the left leg in the standing-leg period t=s3 to s6 converges or approaches asymptotically to zero in the fourth designated period t=s4 to s5.

The greatest value or the maximum value of the assisting force T in each of the third designated period t=s0 to s1 and s3 to s4 is adjusted so that the overlapping period of the standing-leg period of each leg becomes zero.

The temporal change manner of the motive power of the actuator 12R may be controlled such that the assisting force $T_R$ of the right leg in the lifted-leg period t=s3 to s6 indicates the greatest value or the maximum value in the fifth designated period t=s5 to s6 (refer to the dashed line). The fifth designated period t=s5 to s6 is a period after the right leg transits from the bending motion state to the stretching motion state, until it becomes the standing-leg state.

The temporal change manner of the motive power of the actuator 12L may be controlled such that the assisting force $T_L$ of the left leg in the lifted-leg period t=s0 to s3 indicates the greatest value or the maximum value in the fifth designated period t=s2 to s3 (refer to the dashed line). The fifth designated period t=s2 to s3 is a period after the left leg transits from the bending motion state to the stretching motion state, until it becomes the standing-leg state.

In place of the assisting force T, a work (a product of the assisting force (torque) and the variation amount of the hip joint angle) may be controlled so as to temporally change according to the above described manner.

Effect

Second Embodiment

According to the walking motion assist device 10 of the present invention, each length (long/short) of the third designated period t=s0 to s1 (or s3 to s4) and the fourth designated period t=s1 to s2 (or s4 to s5) is adjusted (refer to the one-dot chain line and the two-dot chain line of FIG. 11). By this, in the third designated period t=s0 to s1, the center of gravity $P_G$ of the human P is displaced to the right side from the original position (the origin position of the XY plane (horizontal plane) of the human coordinate system) (refer to t=s1 of FIG. 10). As a result, the bending motion of the left leg can be prompted (refer to t=s1 of FIG. 9). Similarly, in the third designated period t=s3 to s4, the center of gravity $P_G$ of the human P is displaced to the left side from the original position (refer to t=s4 of FIG. 10). As a result, the bending motion of the right leg can be prompted (refer to t=s4 of FIG. 9).

On the other hand, in the fourth designated period t=s1 to s2, the center of gravity $P_G$ of the human P can be displaced to the left side, that is, towards the original position (refer to t=s2 of FIG. 10). Similarly, in the fourth designated period t=s4 to s5, the center of gravity $P_G$ of the human P can be displaced to the right side, that is, towards the original position (refer to t=s2 of FIG. 10). As a result of these, the displacement amount of the center of gravity of the creature is limited, and enables to avoid a situation in which the posture thereof becomes unstable.

By controlling the operation of each of the pair of actuators 12 so that each length of the third designated period t=s0 to s1 (or s3 to s4) and the fourth designated period t=s1 to s2 (or t=s4 to s5) is calculated, the swinging range of the center of gravity $P_G$ of the human P in the right and left direction is restricted from the view point of stabilizing the posture, while smoothening the walking motion thereof.

In a case where the right leg is in the standing-leg state and the left leg is in the lifted-leg state, and in a case where the left leg is in the standing-leg state and the right leg is in the lifted-leg state, each of the third designated period and the fourth designated period may be adjusted to a different length. By doing so, symmetry or asymmetry of the swinging manner of the center of gravity $P_G$ of the human P in the right and left direction may be controlled (refer to FIG. 10). For example, even in a case where the motion capability of the pair of right and left legs differ, the swinging manner of the center of gravity $P_G$ of the human P in the right and left direction can be controlled symmetrically. Therefore, smoothening of the walking motion can be attained while stabilizing the posture of the human P.

In the third designated period of the right leg of the human P, the translation of the body derived from the floor reaction force acting on the right leg is largely prompted compared to other periods of the standing-leg period (refer to t=s0 to t=s1 of FIG. 9 and FIG. 11). In the third designated period of the left leg of human P, the translation of the body derived from the floor reaction force acting on the left leg is largely prompted compared to other periods of the standing-leg period (refer to t=s3 to t=s4 of FIG. 9 and FIG. 11). Since the third designated period of one leg overlaps a period immediately after the other leg transits from the standing-leg state to the lifted-leg state, smooth bending motion of the other leg is facilitated so as to follow the translation of the body.

In the middle period or the later period t=s1 to s2 of the standing-leg period of the right leg, the right leg becomes in a state capable of moving without being restricted by the operation of the actuator 12R (refer to the one-dot chain line of FIG. 11). Similarly, in the middle period or the later period t=s4 to s5 of the standing-leg period of the left leg, the left leg becomes in a state capable of moving without being restricted by the operation of the actuator 12L (refer to the two-dot chain line of FIG. 11). Therefore, in the third designated period t=s0 to s1 or t=s3 to s4 of each leg, following the translation of the body being relatively largely facilitated as described above, a smooth bending motion of each of the legs is facilitated (refer to t=s0 to s1 and s3 to s4 of FIG. 9).

The greatest value or the maximum value of the assisting force T in the third designated period t=s0 to s1 or t=s3 to s4 is adjusted so that the overlapping period of the standing-leg period of each of the legs approaches zero. By doing so, it is able to uniformly shorten a both-legs-supported period in which both of the legs are in the standing-leg state, even if the followability of the floor leaving motion of the leg associated with the translation of the body is right-left asymmetry or different due to an individual difference of the creature. Therefore, in the standing-leg period of one leg, a situation in which the other leg is dragged due to delay of floor leaving of the other leg is avoided.

The assisting force $T_R$ of the right leg in the lifted-leg period is adjusted so as to indicate the greatest value or the maximum value in the fifth designated period t=s5 to s6 (refer to the dashed line of FIG. 11). The assisting force $T_L$ of the left leg in the lifted-leg period is adjusted so as to indicate the greatest value or the maximum value in the fifth designated period t=s2 to s3 (same as above). By doing so, in the fifth designated period of one leg, the translation of the body derived from the floor reaction force acting on the one leg is more prompted compared to other periods in the lifted-leg period. As a result, the floor reaction force acting on the one leg is increased immediately after the start of the third designated period continuing from the fifth designated period of the one leg, and the translation of the body in the third designated period is further more facilitated as described above, and a smooth bending motion of the other leg is further facilitated.

EXAMPLES

Second Embodiment

Examples 1 to 4

Each of FIG. 12A to FIG. 12D indicates the measurement result of the temporal change manner of the hip joint angle $\phi$ of the test subject (human P) in a walking motion by receiving assisting force T of the walking motion assist device 10, in each of the examples 1 to 4. Each of FIG. 13A to FIG. 13D indicates the measurement result of a trajectory of a projected position of the center of gravity position of the test subject onto a horizontal plane in the above cases.

In each of the examples 1 to 4, each of a desired phase difference $\delta_L$ between the assisting force $T_L$ of the left leg and the left hip joint angle $\phi_L$, and a desired phase difference $\delta_R$ between the assisting force $T_R$ of the right leg and the right hip joint angle $\phi_R$ was controlled. In each of examples 2 to 4, a weight of 3 kg was attached to the right ankle of the test subject, whereas the weight was not attached to the test subject in example 1.

The phase difference δ between the assisting force T and the hip joint angle ϕ is defined, for example, as a result of converting the difference between the time point when the assisting force T indicates the maximum value at the stretching side (or the bending side) and the time point when the hip joint angle ϕ indicates the maximum value at the stretching side (or the bending side), or the average value of the difference, with reference to a phase variation amount 27π [rad] across a walking motion cycle S of the human P. The phase difference δ is defined as a positive value (+) in a case where the assisting force T is leading in phase than the hip joint angle ϕ, while is defined as a negative value (−) in a case the assisting force T is delayed in phase than the hip joint angle ϕ.

TABLE 2

| Example | Left desired phase difference $\delta_L$ [rad] | Right desired phase difference $\delta_R$ [rad] |
|---|---|---|
| 1 | 0 | 0 |
| 2 | 0 | 0 |
| 3 | +0.4 | −0.4 |
| 4 | −0.4 | +0.4 |

It can be seen from FIG. 12 that the difference of amplitude between the right hip joint angle $\phi_R$ (refer to the one-dot chain line) and the left hip joint angle $\phi_L$ (refer to the two-dot chain line) of the test subject was larger in examples 2 to 4 (refer to FIG. 12B to FIG. 12D) in which the weight was attached to the right ankle of test subject compared to example 1 (refer to FIG. 12A) in which the weight was not attached to the right ankle of the test subject. From FIG. 13, compared to example 1 (refer to FIG. 13A) in which the weight is not attached to the test subject, in examples 2 to 4 (refer to FIG. 3B to 3D) in which the weight is attached to the right ankle of the test subject, the center of gravity position widely swings to the left forward. On the other hand, in all of examples 1 to 4, the center of gravity position pos_yd in the lateral direction is controlled so as to fall within a certain range (−0.015 to 0.015 [m]).

Examples 5 to 7

Figure 14A:
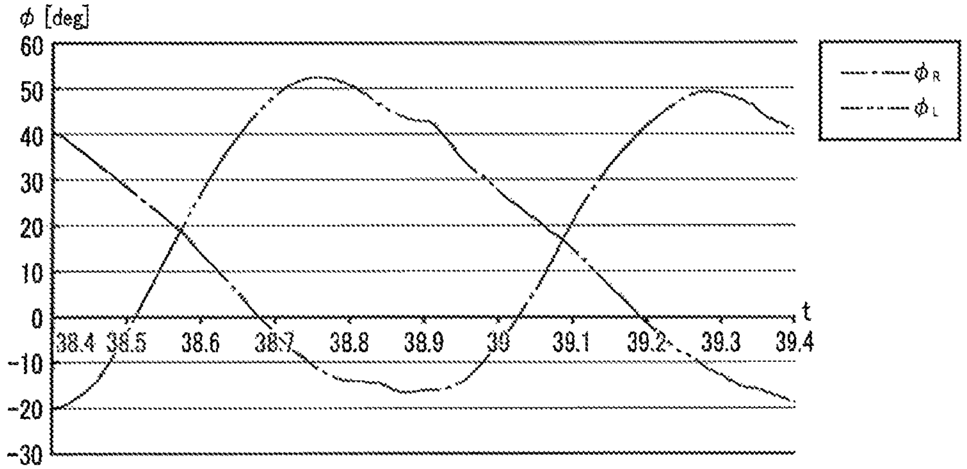
FIG. 14A, FIG. 14B, and FIG. 14C are explanatory diagrams related to temporal change manner of a hip joint angle of examples 5 to 7.
Figure 14B:
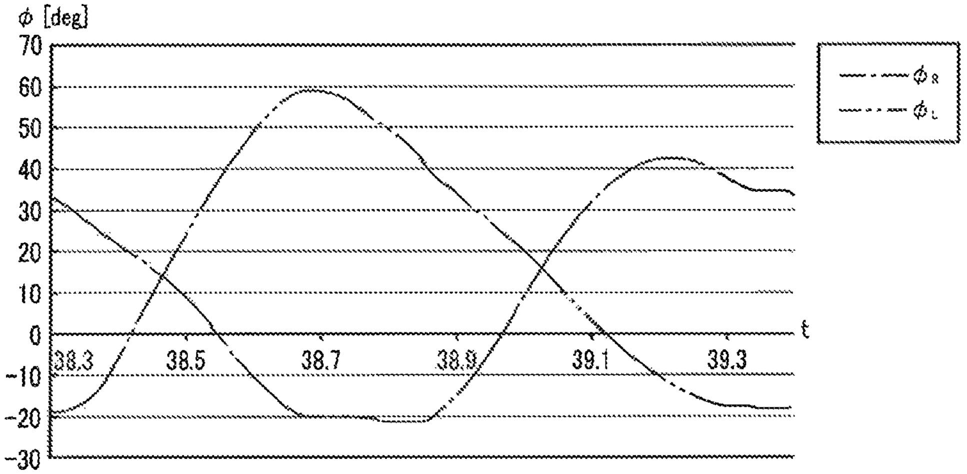
Figure 14C:
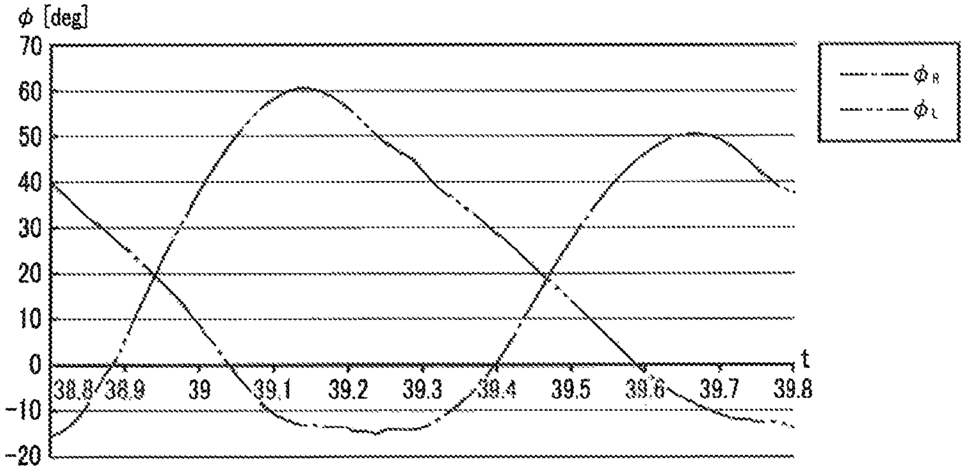

Each of FIG. 14A to FIG. 14C indicates the measurement result of the temporal change manner of the hip joint angle ϕ of the test subject in a walking motion by receiving assisting force T of the walking motion assist device 10, in each of the examples 5 to 7. Each of FIG. 15A to FIG. 15C indicates the measurement result of a trajectory of a projected position of the center of gravity position of the test subject onto a horizontal plane in the above case. Each of FIG. 16A to FIG. 16C indicates a measurement result of the center of gravity position pos_yd of the test subject in the lateral direction.

In each of the examples 5 to 7, the desired phase difference $\delta_L$ between the assisting force $T_L$ of the left leg and the left hip joint angle $\phi_L$ was controlled to −0.4 [rad], and the desired phase difference $\delta_R$ between the assisting force $T_R$ of the right leg and the right hip joint angle $\phi_R$ was controlled to +0.4 [rad]. A weight was attached to the right ankle of the test subject. The assisting force T applied to the test subject was controlled in a temporal change manner as shown in FIG. 17.

Figure 17A:
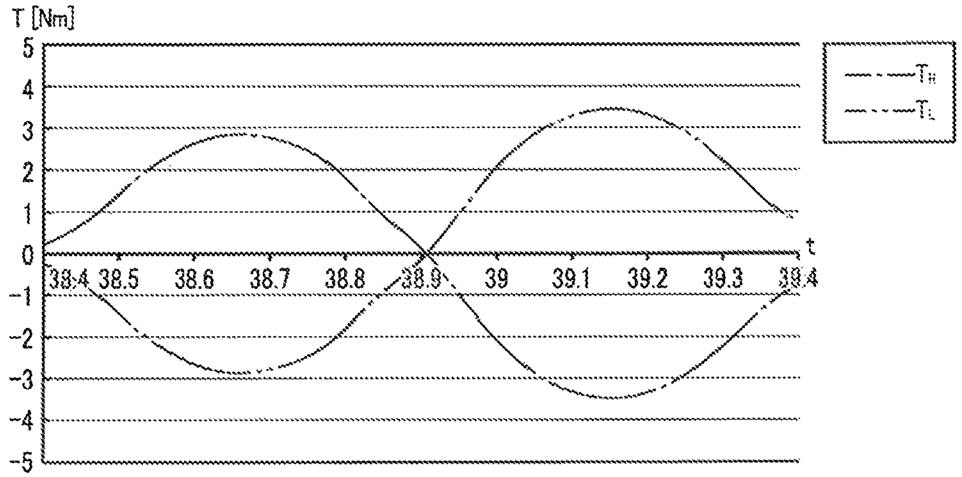
FIG. 17A, FIG. 17B, and FIG. 17C are explanatory diagrams related to temporal change manner of a center of gravity position of examples 5 to 7.

In example 5, as shown in FIG. 17A, the assisting force T is controlled such that the amplitude of the bending motion assisting force $T_R$ (>0) of the right leg with the weight attached is larger than the amplitude of the bending motion assisting force $T_L$ (>0) of the left leg without the weight being attached, while the amplitude of the stretching motion assisting force $T_R$ (<0) of the right leg is smaller than the amplitude of the stretching motion assisting force $T_L$ (<0) of the left leg. By doing so, the influence of the weight with respect to the motion of the right leg is reduced, and the difference of amplitude between the right hip joint angle $\phi_R$ (refer to the one-dot chain line) and the left hip joint angle $\phi_L$ (refer to the two-dot chain line) of the test subject is small to a negligible degree as shown in FIG. 14A.

Figure 17B:
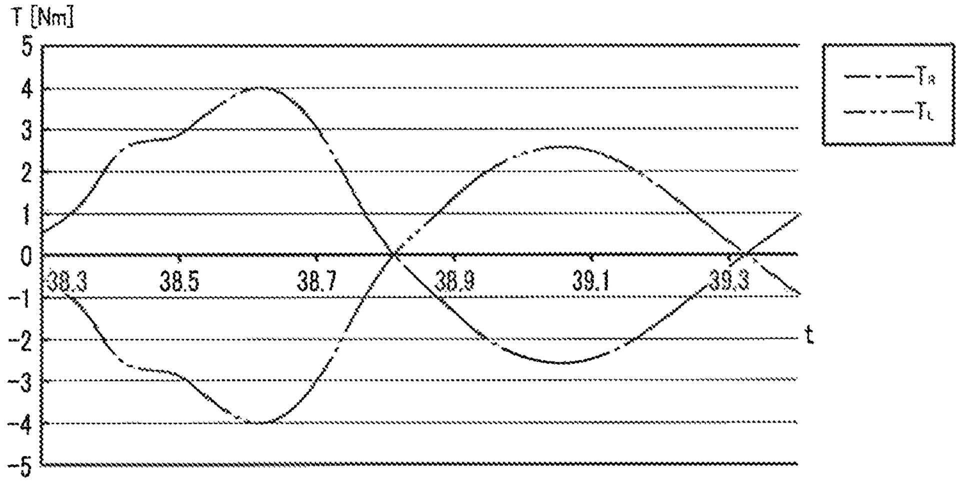

In example 6, as shown in FIG. 17B, the assisting force T is controlled such that the amplitude of the bending motion assisting force $T_R$ of the right leg with the weight attached is smaller than the amplitude of the bending motion assisting force $T_L$ of the left leg without the weight being attached, while the amplitude of the stretching motion assisting force $T_R$ of the right leg is larger than the amplitude of the stretching motion assisting force $T_L$ of the left leg. By doing so, the influence of the weight with respect to the motion of the right leg is amplified, and the amplitude of the right hip joint angle $\phi_R$ of the test subject becomes smaller than the amplitude of the left hip joint angle $\phi_L$ as shown in FIG. 14B.

Figure 17C:
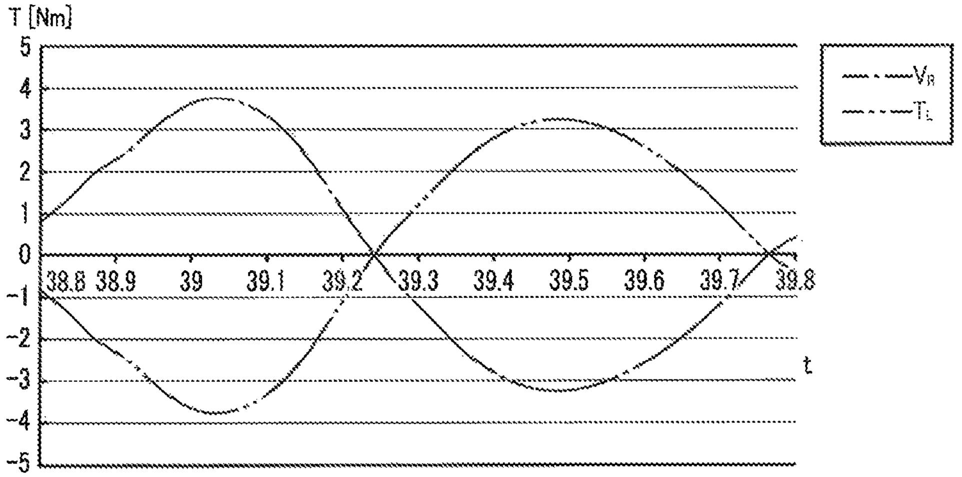

In example 7, as shown in FIG. 17C, the assisting force T is controlled such that the amplitude of the assisting force T of the bending motion and stretching motion of each leg becomes the same degree. By doing so, the influence of the weight with respect to the motion of the right leg is directly reflected, and the amplitude of the right hip joint angle $\phi_R$ of the test subject becomes slightly smaller than the amplitude of the left hip joint angle $\phi_L$ as shown in FIG. 14C. The difference is smaller than example 6.

Figure 15A:
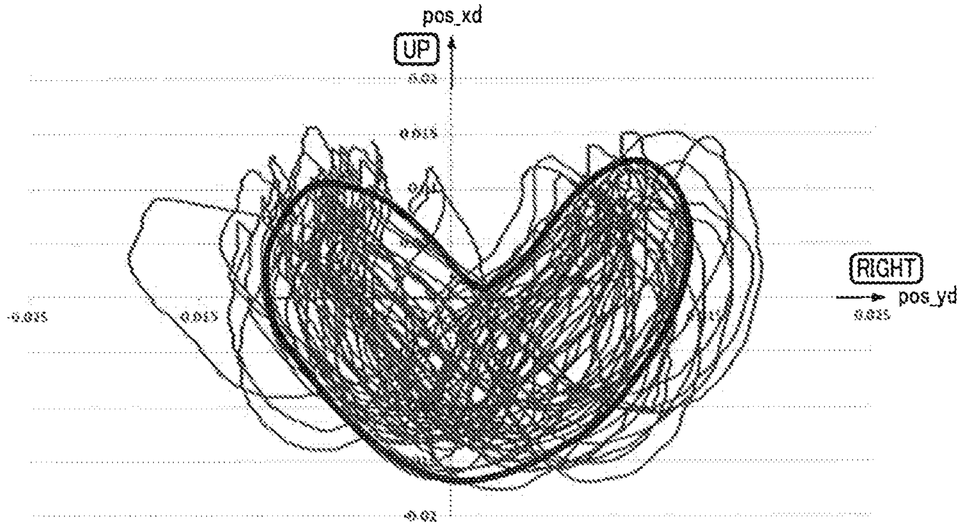
FIG. 15A, FIG. 15B, and FIG. 15C are explanatory diagrams related to a center of gravity position trajectory of examples 5 to 7.
Figure 15B:
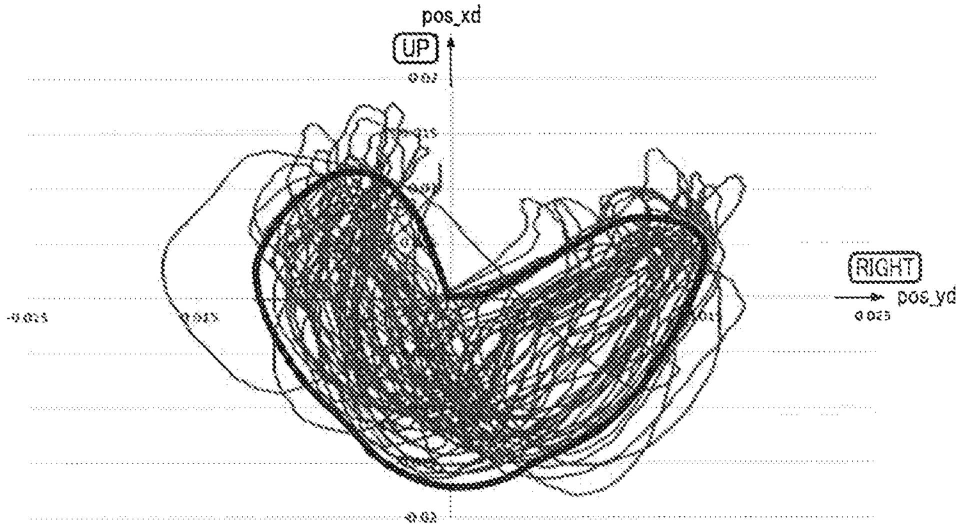
Figure 15C:
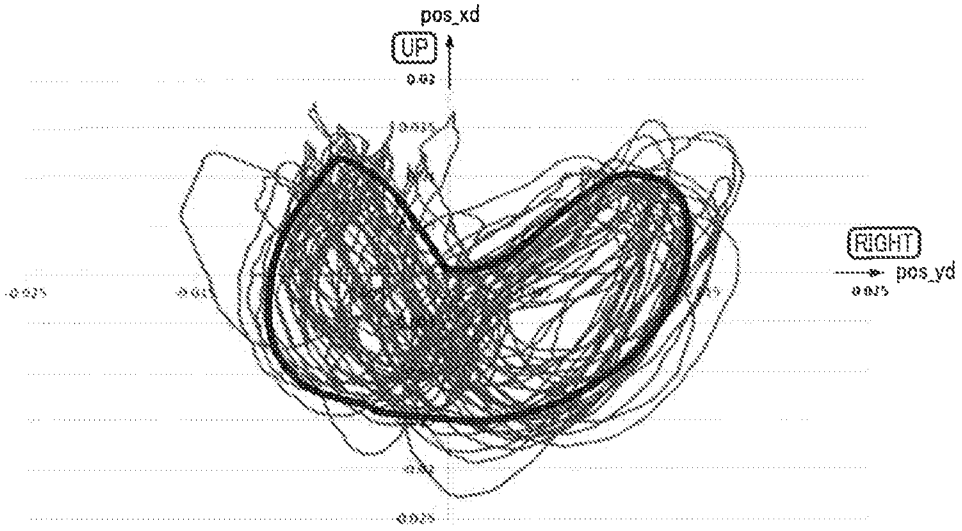
Figure 16A:
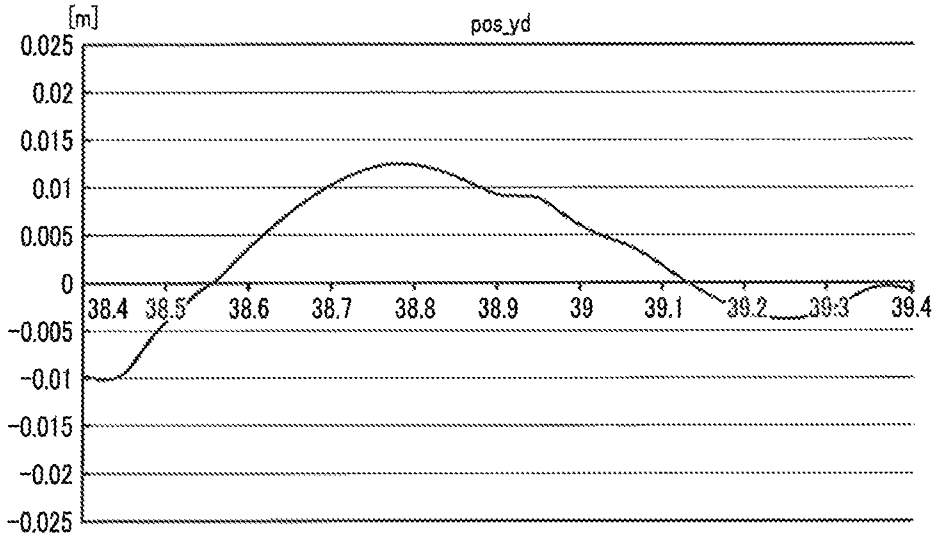
FIG. 16A, FIG. 16B, and FIG. 16C are explanatory diagrams related to temporal change manner of the assisting force of examples 5 to 7.
Figure 16B:
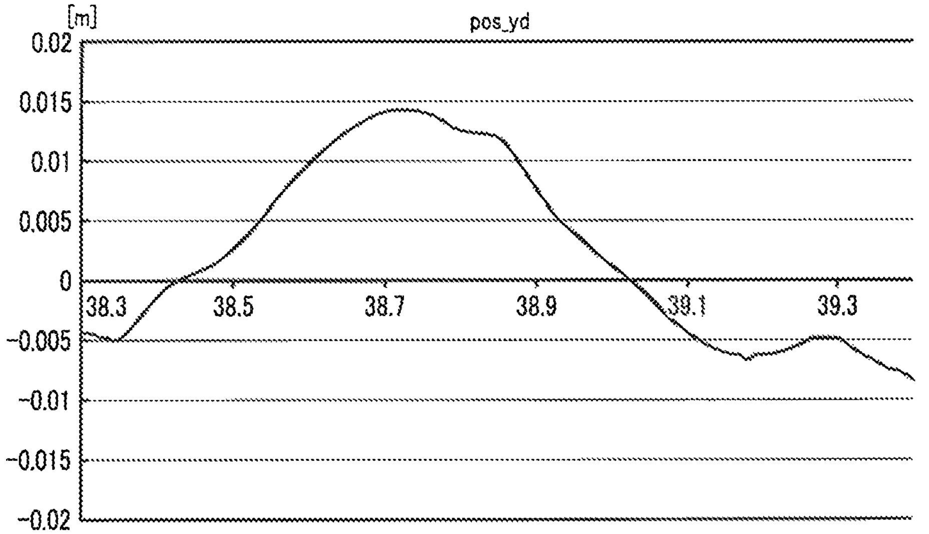
Figure 16C:
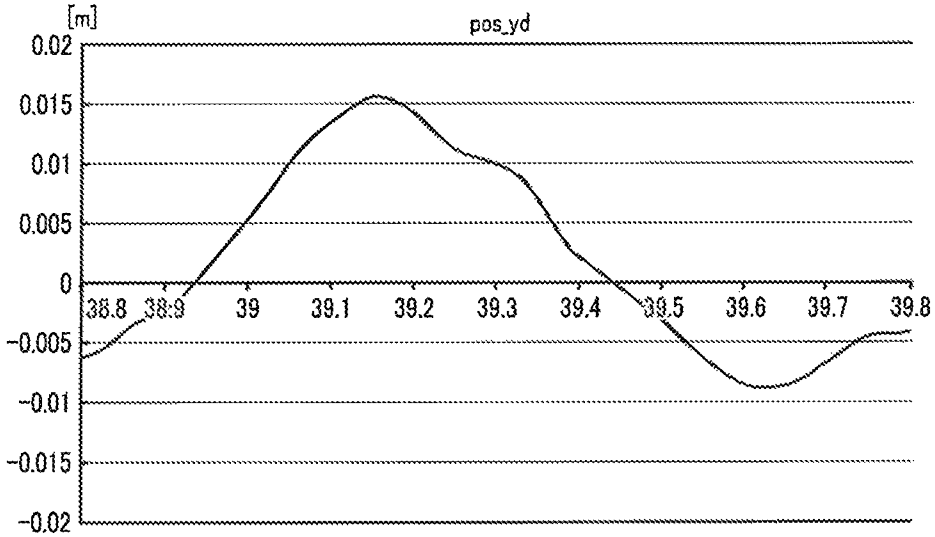

From FIG. 15, compared to example 5 (refer to FIG. 15A) in which the assisting force T is controlled so as to reduce the influence of the weight, in examples 6 and 7 (refer to FIG. 15B and FIG. 15C) in which the assisting force T is controlled such that the influence of the weight is amplified or directly reflected, the center of gravity position widely swings to the left forward. On the other hand, in all of examples 5 to 7, the center of gravity position pos_yd in the lateral direction is controlled so as to fall within a certain range (−0.015 to +0.015 [m]) as shown in FIG. 16A to FIG. 16C.

What is claimed is:

1. A walking motion assist device, comprising:

an attachment adapted to be attached to a body and a leg of a creature;

a hip joint angle sensor configured to output a signal indicating a hip joint angle of the leg of the creature;

an actuator configured to transfer motive power to the attachment; and a controller configured to control an operation of the actuator, which is configured to assist a walking motion of the creature by acting the motive power of the actuator on the creature via the attachment, wherein the controller is configured to, based on a temporal change manner of the hip joint angle indicated by the output signal of the hip joint angle sensor, determine a distinction between a bending motion state and a stretching motion state of the leg, and also determine a distinction between a standing-leg state and a lifted-leg state, and to control a temporal change manner of the motive power of the actuator so that an assisting force or a work in a standing-leg period of the leg indicates a greatest value or a maximum value in a first designated period which is a period from starting of a stretching motion of the leg until a posture thereof coincides with a posture of a basic frontal plane, and then the assisting force or the work monotonously decreases and converges or approaches asymptotically to a predetermined value and then maintains at the predetermined value until the standing-leg period terminates, and wherein the controller is configured to control the temporal change manner of the motive power of the actuator so that the assisting force or the work in a lifted-leg period of the leg indicates a greatest value or a maximum value in a second designated period which is a period from a transition of the leg to the stretching motion state from the bending motion state, until it becomes the standing-leg state.

2. The walking motion assist device according to claim 1, wherein the controller is configured to control the temporal change manner of the motive power of the actuator so that the assisting force or the work in the lifted-leg period of the leg assists a bending motion in a period in which the leg is in the bending motion state.

3. The walking motion assist device according to claim 1, wherein the controller is configured to adjust the greatest value or the maximum value of the assisting force or the work in the first designated period so that an overlapping period of the standing-leg period of each of a pair of right and left legs of the creature approaches zero.

4. A walking motion assist device, comprising:

an attachment adapted to be attached to a body and each of a pair of right and left legs of a creature;

a pair of actuators configured to transfer motive power to the attachment; and a controller configured to control an operation of each of the pair of actuators, which is configured to assist a walking motion of the creature by acting the motive power of the pair of actuators on the creature via the attachment, wherein the controller is configured to control a temporal change manner of the motive power of the actuator so as to adjust a length of each of a third designated period and a fourth designated period, in a case where an assisting force is acted in a stretching direction of one leg in a standing-leg state among the pair of right and left legs and the assisting force is acted in a bending direction of another leg in a lifted-leg state, the third designated period being a period in which the assisting force acting on the one leg is stronger than the assisting force acting on the other leg, and the fourth designated period being a period subsequent to the third designated period and in which the assisting force acting on the other leg is stronger than the assisting force acting on the one leg, wherein the controller is configured to control the temporal change manner of the motive power of the actuators so that the assisting force or a work in a lifted-leg period of the other leg indicates a greatest value or a maximum value in a fifth designated period which is a period from a transition of the other leg to a stretching motion state from a bending motion state, until it becomes the standing-leg state.

5. The walking motion assist device according to claim 4, wherein the controller is configured to control the temporal change manner of the motive power of the actuators so that each of the third designated period and the fourth designated period becomes a different length, in a case where the one leg is the right leg and the other leg is the left leg, and in a case where the one leg is the left leg and the other leg is the right leg.

6. The walking motion assist device according to claim 4, wherein the controller is configured to control the temporal change manner of the motive power of the actuators so that the assisting force or a work in a standing-leg period of the one leg indicates a greatest value or a maximum value in the third designated period.

7. The walking motion assist device according to claim 6, wherein the controller is configured to control the temporal change manner of the motive power of the actuators so that the assisting force or the work in the standing-leg period of the one leg converges or approaches asymptotically to zero in the fourth designated period.

8. The walking motion assist device according to claim 4, wherein the controller is configured to adjust a greatest value or a maximum value of the assisting force or a work in the third designated period so that an overlapping period of a standing-leg period of each of the pair of right and left legs approaches zero.

* * * * *